(12) United States Patent
Strasser et al.

(10) Patent No.: US 7,572,900 B2
(45) Date of Patent: Aug. 11, 2009

(54) BCL-2-MODIFYING FACTOR (BMF) SEQUENCES AND THEIR USE IN MODULATING APOPTOSIS

(75) Inventors: Andreas Strasser, Ascot Vale (AU); Hamsa Puthalakath, Keilor East (AU); Andreas Villunger, Williamstown (AU); Leigh Coultas, Brunswick East (AU); Jennifer Beaumont, Dianella (AU); Lorraine Ann O'Reilly, Cheltenham (AU); David Ching Siang Huang, Fitzroy (AU)

(73) Assignee: The Walter And Eliza Hall Institute of Medical Research, Parkville, Victoria (AU)

( * ) Notice: Subject to any disclaimer, the term of this patent is extended or adjusted under 35 U.S.C. 154(b) by 0 days.

(21) Appl. No.: 10/479,307

(22) PCT Filed: May 30, 2002

(86) PCT No.: PCT/AU02/00693

§ 371 (c)(1),
(2), (4) Date: Jun. 30, 2004

(87) PCT Pub. No.: WO02/097094

PCT Pub. Date: Dec. 5, 2002

(65) Prior Publication Data

US 2005/0064593 A1   Mar. 24, 2005

(30) Foreign Application Priority Data

May 30, 2001   (AU) ..................................... PR5351

(51) Int. Cl.
C07H 21/04   (2006.01)
(52) U.S. Cl. .................................................... 536/23.1
(58) Field of Classification Search ...................... 435/6; 536/23.1
See application file for complete search history.

(56) References Cited

OTHER PUBLICATIONS

Yuan, S-M., et al. 1998 Proteins 30: 136-143.*
Sergel, T.A., et al. 2000 Journal of Virology 74(11): 5101-5107.*
Seffernick, J.L., et al. 2001 Journal of Bacteriology 183(8): 2405-2410.*

H. Puthalakath, et al., "Bmf: A Proapoptotic BH3-Only Protein Regulated by Interaction with the Myosin V Actin Motor Complex, Activated by Anoikis", *Science*, vol. 293, pp. 1829-1832, (Sep. 2001).
EMBL Database Accession No. AK024472. *Homo sapiens* mRNA for FLJ00065 protein. Sep. 29, 2000. & GenPept database No. BAB15762. See whole document, the sequence shows 100% homology with SEQ ID No. 4, 6 and 8 and 87% homology with SEQ ID No. 2.
EMBL Database Accession No. AC025429. *Homo sapiens* chromosome 15 clone CTD-2006D8 map 15q14. Mar. 15, 2000. See whole document, the sequence shows 100% homology with SEQ ID No. 4, 6 and 8 and 87% homology with SEQ ID No. 2.
GenBank Database Accession Nos. AY029253, AY029254 and GenPept database Accession Nos. AAK38747 and AAK38748, respectively. See whole document, Mus musculus Bmf sequences are 100% identical to SEQ ID Nos. 1, 2, 5-8 and *Homo sapiens* BMF sequences are 100% identical to SEQ ID Nos. 3-8.
GenBank Database Accession No. AF506761. Rattus norvegicus Bcl-2 modifying factor (Bmf), mRNA. May 16, 2002 and GenPept Database Accession No. AAM28890. See whole document, sequence is up to 96% identical to SEQ ID Nos. 1-8.

* cited by examiner

*Primary Examiner*—Maryam Monshipouri
*Assistant Examiner*—Marsha M Tsay
(74) *Attorney, Agent, or Firm*—Scully, Scott, Murphy & Presser, P.C.

(57) ABSTRACT

The present invention relates generally to novel molecules capable of, inter alia, modulating apoptosis in mammalian cells and to genetic sequences encoding same. More particularly, the present invention relates to a novel member of the Bcl-2 family of proteins, referred to herein as "Bmf", and to genetic sequences encoding same and to regulatory sequences such as a promoter sequence directing expression of Bmf. Bmf comprises a BH3 domain which facilitates interaction to pro-survival Bcl-2 family members thereby triggering apoptosis. Bmf is regarded, therefore, as a BH3-only molecule. The molecules of the present invention are useful, for example, in therapy, diagnosis, antibody generation and as a screening tool for therapeutic agents capable of modulating physiological cell death or survival and/or modulating cell cycle entry. The present invention further contemplates genetically modified animals in which one or both alleles of Bmf are mutated or partially or wholly deleted alone or in combination with a mutation in one or both alleles of another Bcl-2-type molecule such as but not limited to Bim. The genetically modified animals are useful inter alia in screening for agents which ameliorate the symptoms of diseases caused by defects in apoptosis or which specifically promote apoptosis of target cells.

6 Claims, 11 Drawing Sheets

MERSQCVEELEDDVFQREDGERVTQPGSLLSADLFAQSLLDCPLSRLQLFPLTHCCGPGLRPISQEDKATQTLSP human
MEPPQCVEELEDDVFQSEDGEPGTQPGGLLSADLFAQSQLDCPLSRLQLFPLTHCCGPGLRPISQEDKATQTLSP mouse ASPSQGVMLPCGVTEEPQRLFYGNAGYRLPLPASFPAVLPIGEQPPEGQWI-QHQAEVQIARKLQCIADQFHRL human
ASPSQGVMLPCGVTEEPQRLFYGNAGYRLPLPASFPAGSPLGEQPPEGQ FLQHRAEVQIARKLQCIADQFHRL mouse HVQQHQQNQNRVIWVQILLFLPNLALNGEENRTGAGPR human
HTQQHQQNRDRAWWQVFLFLQNLALNRQENREGVGPW mouse

Figure 1A

| I A R K L Q C I A D Q F H R L | Bmf |
| I A Q E L R R I G D E F N A Y | Bim |
| I G S K L A A M C D D F D A Q | EGL-1 |
| V G R Q L A I I G D D I N R R | Bak |
| L S E C L K R I G D E L D S N | Bax |
| L A L R L A C I G D E M D V S | Bid |
| L A L R L A C I G D E M D V S | Bik |
| T A A R L K A L G D E L H Q R | Hrk |
| Y G R E L R R M S D E F V D S | Bad |

Figure 1B

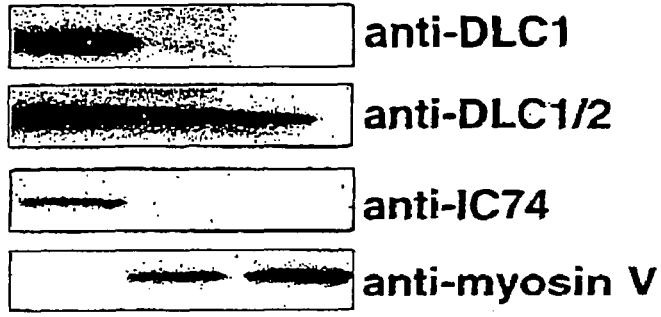
Figure 3E
Figure 3D
Figure 3F

BCL-2-MODIFYING FACTOR (BMF) SEQUENCES AND THEIR USE IN MODULATING APOPTOSIS

This application is a §371 application of International Application PCT/AU02/00693, filed on May 30, 2002.

FIELD OF THE INVENTION

The present invention relates generally to novel molecules capable of, inter alia, modulating apoptosis in mammalian cells and to genetic sequences encoding same. More particularly, the present invention relates to a novel member of the Bcl-2 family of proteins, referred to herein as "Bmf", and to genetic sequences encoding same and to regulatory sequences such as a promoter sequence directing expression of Bmf. Bmf comprises a BH3 domain which facilitates interaction- to pro-survival Bcl-2 family members thereby triggering apoptosis. Bmf is regarded, therefore, as a BH3-only molecule. The molecules of the present invention are useful, for example, in therapy, diagnosis, antibody generation and as a screening tool for therapeutic agents capable of modulating physiological cell death or survival and/or modulating cell cycle entry. The present invention further contemplates genetically modified animals in which one or both alleles of Bmf are mutated or partially or wholly deleted alone or in combination with a mutation in one or both alleles of another Bcl-2-type molecule such as but not limited to Bim. The genetically modified animals are useful inter alia in screening for agents which ameliorate the symptoms of diseases caused by defects in apoptosis or which specifically promote apoptosis of target cells.

BACKGROUND OF THE INVENTION

Reference to any prior art in this specification is not, and should not be taken as, an acknowledgment or any form of suggestion that this prior art forms part of the common general knowledge in any country.

Apoptosis, the physiologic and genetically modulated process of cell death, is of central importance for modeling tissues and maintaining homeostasis in multicellular organisms (Kerr et al., *Br. J. Cancer* 26: 239-257, 1972; Jacobson et al., *Cell* 88: 347-354, 1997). Great progress is being made towards understanding the biochemistry underlying this intrinsic suicide program. The cellular apoptotic effector molecules include a set of cysteine proteinases, termed caspases, that degrade critical cellular substrates (Nicholson et al., *Trends Biochem. Sci.* 22: 299-306, 1997). The regulatory machinery that governs the activation of the caspases is less well understood. However, a family of proteins of which Bcl-2 is the prototypic molecule (and is referred to as the Bcl-2 family of proteins) plays a central role (Jacobson, *Curr. Biol.* 7: R277-R281, 1997; Reed, *Nature* 387: 773-776, 1997; Kroemer, *Nature Med.* 3: 614-620, 1997; Adams and Cory, *Science* 281: 1322-1326, 1998).

Bcl-2 was the first intracellular regulator of apoptosis to be identified (Vaux et al., *Nature* 335: 440-442, 1988) and high levels enhance cell survival under diverse cytotoxic conditions. Other cellular homologs, such as BCl-$x_L$ (Boise et al., *Cell* 74: 597-608, 1993) and Bcl-w (Gibson et al., *Oncogene* 13: 665675, 1996), also enhance cell survival, as do more distantly related viral homologs, such as the adenovirus E1B 19K protein (White et al., *Mol. Cell. Biol.* 12: 2570-2580, 1992) and Epstein-Barr virus BHRF-1 (Henderson et al., *Proc Natl. Acad. Sci. USA* 90: 8479-8483, 1993).

Pro-apoptotic BH3-only members of the Bcl-2 family are essential for initiation of apoptosis in species as distantly related as mice and *C. elegans* (Huang and Strasser, *Cell* 103: 839, 2000). EGL-1, the so far only recognized BH3-only protein in *C. elegans*, is required for all developmentally programmed cell deaths in this organism. In contrast, a number of BH3-only proteins have already been identified in mammals: Blk, Bad, Bik, Hrk, Bid, Bim, Noxa and Puma. Experiments with knock-out mice have shown that different apoptotic stimuli require distinct BH3-only proteins for their initiation. (Huang and Strasser, 2000, supra). For example, Bim is essential for apoptosis induced by cytokine withdrawal or antigen receptor stimulation, but is dispensable for cell death induced by glucocorticoids (Bouillet et al., *Science* 286: 1735, 1999; Bouillet et al., *Nature* 415, 922, 2002). In contrast, Bid is involved in Fas-induced killing of hepatocytes (Yin et al., *Nature* 400: 886, 1999). Moreover, different cell types may require distinct BH3-only proteins for their developmentally programmed death. Consistent with this idea, Bim-deficient mice have an abnormal accumulation of lymphoid and myeloid cells but erythropoiesis appears normal (Bouillet et al., 1999, supra). These results indicate that individual mammalian BH3-only proteins have specific functions.

The pro-apoptotic activity of BH3-only proteins is subject to stringent control. In *C. elegans*, EGL-1 is regulated by the transcriptional represser TRA-1A in a group of neurons that is required for egg-laying (Conradt and Horvitz, *Cell* 93: 519, 1998). Some mammalian BH3-only proteins are also subject to transcriptional regulation. For example, Noxa was discovered as a p53-inducible gene and is therefore a prime candidate for mediating DNA damage-induced apoptosis (Oda et al., *Science* 288: 1053, 2000). Several mammalian BH3-only proteins can also be regulated post-translationally (Huang and Strasser, 2000, supra). In growth factor-stimulated cells, Bad is phosphorylated and sequestered away from pro-survival Bcl-2 family members by binding to 14-3-3 scaffold proteins (Zha et al, *Cell* 87: 619, 1996). In healthy cells, Bim is sequestered to the microtubular dynein motor complex by binding to dynein light chain, DLC1/LC8 (Puthalakath et al., *Mol. Cell* 3: 287, 1999). Certain apoptotic stimuli, such as UV-radiation or treatment with taxol, free Bim (still bound to DLC1) and allow it to translocate to, bind and inactivate pro-survival Bcl-2 family members. This process occurs independently of the cell death executioner cysteine proteases (caspases) and therefore constitutes an upstream signalling event in apoptosis (Puthalakath et al., 1999, supra). In contrast, the pro-apoptotic activity of Bid is unleashed upon cleavage by a variety of caspases (e.g. caspase-8) or by the serine protease granzyme B (Li et al., *Cell* 94: 491-501, 1998; Luo et al., *Cell* 94: 481-490, 1998), indicating that it functions as part of an amplification mechanism rather than as an initiator of apoptosis. These observations demonstrate that through sequestration to specific sites in the cell, different BH3-only proteins function as sensors for distinct forms of intracellular stress.

In work leading to the present invention, the inventors sought novel BH3-only proteins which played a role in embryogenesis. In accordance with the present invention, the inventors cloned "Bmf" (Bcl-2 modifying factor) which was identified through yeast 2-hybrid screening of a day 17 mouse embryonic library using Mcl-1 as bait. Bmf is proposed to induce cell death and act as a "death-ligand" for certain or all members of the pro-survival Bcl-2 family. The identification of this new gene permits the identification and rational design of a range of products for use in therapy, diagnosis, antibody generation and involving modulation of physiological cell death. These therapeutic molecules may act as either, antagonists or agonists of Bmf's friction and will be useful in cancer, autoimmune or degenerative disease therapy.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A sequence listing is provided after the claims.

Specific mutations in an amino acid sequence are represented herein as "$X_1 n X_2$" where $X_1$ is the original amino acid residue before mutation, n is the residue number and $X_2$ is the mutant amino acid. Reference to Xn is a reference to a particular amino acid in an amino acid sequence where X is the amino acid and n is the residue number. The abbreviation X may be to the three letter or single letter amino acid code.

The present invention is predicated in part on the identification of a novel member of the pro-survival Bcl-2 family. This protein is referred to herein as "Bcl-2 modifying factor" or "Bmf". The protein was identified by yeast 2-hybrid screening of a mouse embryonic library using Mcl-1 as bait. Bmf is an apoptosis-inducing BH3-only protein and is activated by anoikis.

Accordingly, one aspect of the present invention provides a nucleic acid molecule comprising a nucleotide sequence encoding a polypeptide having one or more of the identifying characteristics of Bmf or a derivative or homolog thereof.

Another aspect of the present invention provides a nucleic acid molecule comprising a nucleotide sequence encoding or complementary to a sequence encoding an no acid sequence substantially as set forth in one of SEQ ID NO:2 or SEQ ID NO:4 or SEQ ID NO:6 or SEQ ID NO:8 or a derivative or homolog thereof or having at least about 45% or greater similarity to one or more of SEQ ID NO:2 or SEQ ID NO:4 or SEQ ID NO:6 or SEQ ID NO:8 or a derivative or homolog thereof.

Yet another aspect of the present invention contemplates a nucleic acid molecule comprising a nucleotide sequence substantially as set forth in one of SEQ ID NO:1 or SEQ ID NO:3 or SEQ ID NO:5 or SEQ ID NO:7 or a derivative or homolog thereof capable of hybridising to one of SEQ ID NO:1 or SEQ ID NO:3 or SEQ ID NO:5 or SEQ ID NO:7 under low stringency conditions and which encodes an amino acid sequence corresponding to an amino acid sequence set forth in one of SEQ ID NO:2 or SEQ ID NO:4 or SEQ ID NO:6 or SEQ ID NO:8 or a sequence having at least about 45% similarity to one or more of SEQ ID NO:2 or SEQ ID NO:4 or SEQ ID NO:6 or 8.

Still yet another aspect of the present invention contemplates a nucleic acid molecule comprising a sequence of nucleotides substantially as set forth in SEQ ID NOS:1 or SEQ ID NO:3 or SEQ ID NO:5 or SEQ ID NO:7.

Still another aspect of the present invention is directed to an isolated nucleic acid molecule encoding bmf or a derivative thereof, said nucleic acid molecule selected from the list consisting of:—

(i) a nucleic acid molecule comprising a nucleotide sequence encoding the amino acid sequence set forth in one of SEQ ID NO:2 or SEQ ID NO:4 or SEQ ID NO:6 or SEQ ID NO:8 or a derivative or homolog thereof or having at least about 45% similarity to one or more of SEQ ID NO:2 or SEQ ID NO:4 or SEQ ID NO:6 or SEQ ID NO:8;

(ii) a nucleic acid molecule comprising a nucleotide sequence substantially as set forth in one of SEQ ID NO:1 or SEQ ID NO:3 or SEQ ID NO:5 or SEQ ID NO:7 or a derivative or homolog thereof;

(iii) a nucleic acid molecule capable of hybridizing under low stringency conditions to the nucleotide sequence substantially as set forth in one of SEQ ID NO:1 or SEQ ID NO:3 or SEQ ID NO:5 or SEQ ID NO:7 a derivative or homolog and encoding an amino acid sequence corresponding to an amino acid sequence as set forth in one of SEQ ID NO:SEQ ID NO:2 or SEQ ID NO:4 or SEQ ID NO:6 or SEQ ID NO:8 a derivative or homolog, or a sequence having at least about 45% similarity to one or more of SEQ ID NO:2 or SEQ ID NO:4 or SEQ ID NO:6 or SEQ ID NO:8;

(iv) a nucleic acid molecule capable of hybridizing to the nucleic acid molecule of paragraphs (i) or (ii) or (iii) under low stringency conditions and encoding an amino acid sequence having at least about 45% similarity to one or more of SEQ ID NO:2 or SEQ ID NO:4 or SEQ ID NO:6 or SEQ ID NO:8; and (v) a derivative or mammalian homolog of the nucleic acid molecule of paragraphs (i) or (ii) or (iii) or (iv).

A further aspect of the present invention is directed to an isolated polypeptide selected from the list consisting of:—

(i) a polypeptide having an amino acid sequence substantially as set forth in one of SEQ ID NO:2 or SEQ ID NO:4 or SEQ ID NO:6 or SEQ ID NO:8 or derivative or homolog thereof or a sequence having at least about 45% similarity to one or more of SEQ ID NO:2 or SEQ ID NO:4 or SEQ ID NO:6 or SEQ ID NO:8;

(ii) a polypeptide encoded by a nucleotide sequence substantially as set forth in one of SEQ ID NO:1 or SEQ ID NO:3 or SEQ ID NO:5 or SEQ ID NO:7 or derivative or homolog thereof or a sequence encoding an amino acid sequence having at least about 45% similarity to one or more of SEQ ID NO:2 or SEQ ID NO:4 or SEQ ID NO:6 or SEQ ID NO:8;

(iii) a polypeptide encoded by a nucleic acid molecule capable of hybridizing to the nucleotide sequence as set forth in one of SEQ ID NO:1 or SEQ ID NO:3 or SEQ ID NO:5 or SEQ ID NO:7 or derivative or homolog thereof under low stringency conditions and which encodes an amino acid sequence substantially as set forth in SEQ ID NO:2 or SEQ ID NO:4 or SEQ ID NO:6 or SEQ ID NO:8 or derivative or homolog thereof or an amino acid sequence having at least about 45% similarity to one or more of SEQ ID NO:2 or SEQ ID NO:4 or SEQ ID NO:6 or SEQ ID NO:8;

(iv) a polypeptide as defined in paragraphs (i) or (ii) or (iii) in homodimeric form; and (v) a polypeptide as defined in paragraphs (i) or (ii) or (iii) in heterodimeric form.

Yet another aspect of the present invention provides a method of producing a genetically modified non-human animal, said method comprising introducing into embryonic stem cells of an animal a genetic construct comprising a bmf nucleotide sequence carrying a single or multiple nucleotide substitution, addition and/or deletion or inversion or insertion wherein there is sufficient bmf nucleotide sequences to promote homologous recombination with a bmf gene within the genomic of said embryonic stem cells selecting for said homologous recombination and selecting embryonic stem cells which carry a mutated bmf gene and then generating a genetically modified animal from said embryonic stem cell.

Figure 1C:
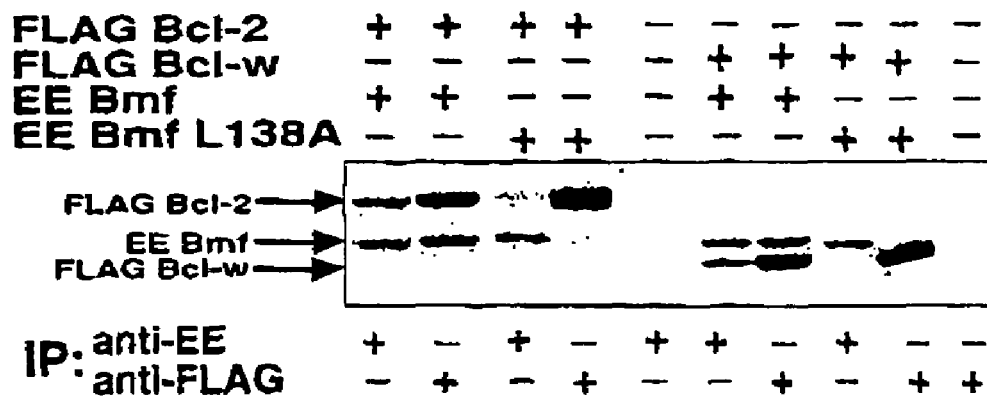
FIG. 1 is a representation showing Bmf, a novel mammalian BH3-only protein. (A) Predicted amino acid sequence of mouse and human Bmf. The nine amino acids that are conserved with the dynein light chain-binding motif of Bim are indicated by a box marked with a single asterisk (*). The short BH3 region, identified by hidden Markov modeling (Krogh et al., *J. Mol. Biol.* 235: 1501, 1994), is indicated by a box marked with two asterisks (**). (B) Alignment of the BH3 region of Bmf with other pro-apoptotic Bcl-2 family members. Black boxes indicate identical amino acids and grey boxes indicate similar residues. (C) Wild-type Bmf, but not a BH3 mutant, binds pro-survival Bcl-2 and Bcl-w. Co-immunoprecipitation experiments were carried out as previously described (Puthalakath et al., 1999, supra). Briefly, 293T cells were transiently co-transfected with expression constructs for FLAG-tagged Bcl-2 (or Bcl-w) and EE(Glu-Glu)-tagged Bmf or L138A mutant Bmf. Cells were metabolically labeled with $^{35}$S-methionine 24 hours after transfection and harvested after overnight culture. Volumes of cell lysates with equivalent trichloroacetic acid (TCA)-precipitable $^{35}$S counts were used for immunoprecipitations with mAbs to the FLAG or EE epitope tags. (D) Interaction of endogenous Bmf with Bcl-2 in MCF-7 cells. Lysates from 107 MCF-7 cells, prepared in lysis buffer containing 1% v/v Triton X-100, were immunoprecipitated either with Bcl-2-100 (anti-human Bcl-2) mAb or an isotype matched control mAb coupled to sepharose. Bound proteins were eluted from the beads by boiling in Laemmli buffer (non reducing), size fractionated on SDS-PAGE and transferred onto nitrocellulose filters. Western blotting was performed with a rat anti-Bmf mAb (9G10). The asterisk (*) indicates the light chain of the mAb used for immunoprecipitation. (E) Wild-type Bmf, but not a BH3 mutant, kills L929 fibroblasts. L929 fibroblasts were transfected with empty vector, expression constructs for hygromycin resistance alone, or with wild-type Bmf, a BH3 mutant (L138A) of Bmf or Bmf lacking its BH3 domain. Transfected cells were plated in medium containing hygromycin and resulting drug-resistant colonies counted after 10-14 days. Values are means (+/−SD) of three independent experiments. (F and G) Expression of Bmf in cell lines and tissues. For Northern blot analysis (F), 4 µg of poly A$^+$ RNA from various cell lines or from mouse embryos (embryonic day 9 to 1-day after birth) were electrophoresed, blotted and probed with a mouse bmf cDNA probe. Probing with a gapdh cDNA clone was used as the loading control. For Western blot analysis (G), 50 µg of total protein from various mouse tissues was size-fractionated by SDS-PAGE, electroblotted onto nitrocellulose filters and probed with affinity-purified rabbit polyclonal antibodies to Bmf. Probing with a monoclonal antibody to HSP70 served as the loading control.

Single and three letter abbreviations used throughout the specification are defined below.

SINGLE AND THREE LETTER AMINO ACID ABBREVIATIONS

| AMINO ACID | THREE-LETTER ABBREVIATION | ONE-LETTER SYMBOL |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Scrine | Ser | S |
| Threonine | Thr | T |
| Tryptophan | Trp | W |
| Tyrosine | Tyr | Y |
| Valine | Val | V |
| Any residue | Xaa | X |

A summary of sequence identifiers is provided below:—

SUMMARY OF SEQENCE IDENTIFIERS

| SEQ ID NO: | DESCRIPTION |
|---|---|
| 1 | Nucleotide sequence of mouse bmf |
| 2 | Amino acid sequence of mouse Bmf |
| 3 | Nucleotide sequence of human bmf |
| 4 | Amino acid sequence of human Bmf |
| 5 | Nucleotide sequence of BH3 domain of mouse bmf |
| 6 | Amino acid sequence of BH3 domain of mouse Bmf |
| 7 | Nucleotide sequence of BH3 domain of human bmf |
| 8 | Amino acid sequence of BH3 domain of human bmf |
| 9 | Nucleotide sequence of mouse bmf promoter |
| 10 | Nucleotide sequence of human bmf promoter |
| 11 | 5' sense primer |
| 12 | 3' antisense primer |
| 13 | internal bmf primer |
| 14 | 5' sense primer |
| 15 | 3' antisense primer |
| 16 | internal primer |
| 17 | predicted amino acid sequence of mouse Bmf |
| 18 | predicted amino acid sequence of human Bmf |
| 19 | partial amino acid sequence of Bmf |
| 20 | partial amino acid sequence of Bim |
| 21 | partial amino acid sequence of EGL-1 |
| 22 | partial amino acid sequence of Bak |
| 23 | partial amino acid sequence of Bax |
| 24 | partial amino acid sequence of Bid |
| 25 | partial amino acid sequence of Bik |
| 26 | partial amino acid sequence of Hrk |
| 27 | partial amino acid sequence of Bad |

DETAILED DESCRIPTION OF THE PREFERRED EMBODIMENTS

The present invention is predicated in part on the identification of a novel member of the Bcl-2 family of proteins. The protein is called "Bmf" for "Bcl-2 modifying factor". It is proposed that in healthy cells, Bmf is sequestered to the actin-based myosin V motor complex by binding to a dynein light chain and in particular dynein light chain 2 (DLC2). It is further proposed that certain apoptotic stimuli, such as anoikis, release Bmf from the myosin V motor complex allowing it to translocate and bind to Bcl-2. Consequently, Bmf functions as a sensor of intracellular damage by sequestration to motor complexes on distinct cytoskeletal structures.

Accordingly, one aspect of the present invention provides a nucleic acid molecule comprising a nucleotide sequence encoding or complementary to a sequence encoding an amino acid sequence substantially as set forth in one of SEQ ID NO:2 or SEQ ID NO:4 or SEQ ID NO:6 or SEQ ID NO:8 or a derivative or homolog thereof or having at least about 45% or greater similarity to one or more of SEQ ID NO:2 or SEQ ID NO:4 or SEQ ID NO:6 or SEQ ID NO:8 or a derivative or homolog thereof.

The term "similarity" as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In a particularly preferred embodiment, nucleotide and sequence comparisons are made at the level of identity rather than similarity.

Terms used to describe sequence relationships between two or more polynucleotides or polypeptides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units, inclusive of nucleotides and amino acid residues, in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerised implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as, for example, disclosed by Altschul et al. (*Nucl. Acids. Res.* 25: 3389, 1997). A detailed discussion of sequence analysis can be found in Unit 19.3 of Ausubel et al ("Current Protocols in Molecular Biology", John Wiley & Sons Inc., 1994-1998, Chapter 15).

The terms "sequence similarity" and "sequence identity" as used herein refers to the extent that sequences are identical or functionally or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) Occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

Another aspect of the present invention contemplates a nucleic acid molecule comprising a nucleotide sequence substantially as set forth in one of SEQ ID NO:1 or SEQ ID NO:3 or SEQ ID NO:5 or SEQ ID NO:7 or a derivative or homolog thereof capable of hybridizing to one of SEQ ID NO:1 or SEQ ID NO:3 or SEQ ID NO:5 or SEQ ID NO:7 under low stringency conditions and which encodes an amino acid sequence corresponding to an amino acid sequence set forth in one of SEQ ID NO:2 or SEQ ID NO:4 or SEQ ID NO:6 or SEQ ID NO:8 or a sequence having at least about 45% similarity to one or more of SEQ ID NO:2 or SEQ ID NO:4 or SEQ ID NO:6 or SEQ ID NO:8.

More particularly, the present invention contemplates a nucleic acid molecule comprising a sequence of nucleotides substantially as set forth in SEQ ID NO:1 or SEQ ID NO:3 or SEQ ID NO:5 or SEQ ID NO:7.

Preferably, the subject nucleic acid molecules encode a polypeptide having the identifying characteristics of Bmf or its homologs or derivatives including functional derivatives.

Reference herein to a low stringency includes and encompasses from at least about 0 to at least about 15% v/v formamide and from at least about 1 M to at least about 2 M salt for hybridization, and at least about 1 M to at least about 2 M salt for washing conditions. Generally, low stringency is at from about 25-30° C. to about 42° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m=69.3+0.41$ (G+C)% (Marmur and Doty, *J. Mol. Biol.* 5: 109, 1962). However, the $T_m$ of a duplex DNA decreases by 1° C. with every increase of 1% in the number of mismatch base pairs (Bonner and Lasky, *Eur. J. Biochem.* 46: 83, 1974). Formamide is optional in these hybridization conditions. Accordingly, particularly preferred levels of stringency are defined as follows: low stringency is 6×SSC buffer, 0.1% w/v SDS at 25-42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C.

The nucleic acid molecule according to this aspect of the present invention corresponds herein to "bmf". This gene has been determined in accordance with the present invention to induce apoptosis. The product of the bmf gene is referred to herein as "Bmf" without limiting this invention in any way, human bmf has been mapped to human chromosome location 15q14. Bmf is known as a "BH3-only" protein since the only Bcl-2 homology region which it contains is BH3. It thereby forms a novel member of a Bcl-2 related BH3-only pro-apoptotic group which also comprises, for example, Bik/Nbk, Bid, Bim and Hrk.

The nucleic acid molecule encoding bmf is preferably a sequence of deoxyribonucleic acids such as cDNA sequence, an mRNA sequence or a genomic sequence. A genomic sequence may also comprise exons and introns. A genomic sequence may also include a promoter region or other regulatory region. The bmf genetic sequence includes splice variants.

Reference hereinafter to "Bmf" and "bmf" should be understood as a reference to all forms of Bmf and bmf, respectively, including, by way of example, polypeptide and cDNA isoforms of bmf which may be identified as arising from alternative splicing of bmf mRNA. Reference hereinafter to Bmf and bmf in the absence of a reference to its derivatives should be understood to include reference to its derivatives thereof including any splice variants.

The protein and/or gene is preferably from a human, primate, livestock animal (e.g. sheep, pig, cow, horse, donkey) laboratory test animal (e.g. mouse, rat, rabbit, guinea pig) companion animal (e.g. dog, cat), captive wild animal (e.g. fox, kangaroo, koala, deer), aves (e.g. chicken, geese, duck, emu, ostrich), reptile or fish.

Derivatives include fragments (such as peptides), parts, portions, chemical equivalents, mutants, homologs or mimetics from natural, synthetic or recombinant sources including fusion proteins. Derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterized by the removal of one or more amino acids from the sequence. Substitutional amino acid variants are those in which at least one residue in the sequence has been removed and a different residue inserted in its place. Additions to amino acid sequences including fusions with other peptides, polypeptides or proteins. Mutants should be understood to include, but is not limited to, the specific Bmf or bmf mutant molecules described herein. Derivatives include, for example, peptides derived from the BH3 region, from the dynein binding region or from a site of phosphorylation. Peptides include, for example, molecules comprising at least 4 contiguous amino acids corresponding to at least 4 contiguous amino acids of Bmf as herein defined. Use of the term "polypeptides" herein should be understood to encompass peptides, polypeptides and proteins.

The derivatives of Bmf include fragments having particular epitopes or parts of the entire Bmf protein fused to peptides, polypeptides or other proteinaceous or non-proteinaceous molecules. For example, Bmf or derivative thereof may be fused to a molecule to facilitate its entry into a cell. Analogues of Bmf contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecules or their analogues. Derivatives of nucleic acid sequences may similarly be derived from single or multiple nucleotide substitutions, deletions and/or additions including fusion with other nucleic acid molecules. The derivatives of the nucleic acid molecules of the present invention include oligonucleotides, PCR primers, antisense molecules, molecules suitable for use in co-suppression and fusion of nucleic acid molecules.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-S-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown in Table 1.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-Nmethylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornilthine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |

TABLE 1-continued

| Non-conventional amino acid | Code | Non-conventional amino acid | Code |
|---|---|---|---|
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmom | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl)carbamylmethyl)glycine | Nnbhm | N-(N-(3,3-diphenylpropyl)carbamylmethyl)glycine | Nnbhe |
| 1-carboxy-1-(2,2-diphenyl-ethylamino)cyclopropane | Nmbc | | |

Crosslinkers can be used, for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The nucleic acid molecule of the present invention is preferably in isolated form or ligated to a vector, such as an expression vector. By "isolated" is meant a nucleic acid molecule having undergone at least one purification step and this is conveniently defined, for example, by a composition comprising at least about 10% subject nucleic acid molecule, preferably at least about 20%, more preferably at least about 30%, still more preferably at least about 40-50%, even still more preferably at least about 60-70%, yet even still more preferably 80-90% or greater of subject nucleic acid molecule relative to other components as determined by molecular weight, encoding activity, nucleotide sequence, base composition or other convenient means. The nucleic acid molecule of the present invention may also be considered, in a preferred embodiment, to be biologically pure.

In a particularly preferred embodiment, the nucleotide sequence corresponding to bmf is a cDNA sequence comprising a sequence of nucleotides as set forth in one of SEQ ID NO:1 or SEQ ID NO:3 or SEQ ID NO:5 or SEQ ID NO:7 or is a derivative or homolog thereof including a nucleotide sequence having similarity to one of SEQ ID NO:1 or SEQ ID NO:3 or SEQ ID NO:5 or SEQ ID NO:7 and which encodes an amino acid sequence corresponding to an amino acid sequence as set forth in one of SEQ ID NO:2 or SEQ ID NO:4 or SEQ ID NO:6 or SEQ ID NO:8 or a sequence having at least about 45% similarity to one or more of SEQ ID NO:2 or SEQ ID NO:4 or SEQ ID NO:6 or SEQ ID NO:8.

A derivative of the nucleic acid molecule of the present invention also includes nucleic acid molecules capable of hybridizing to the nucleotide sequences as set forth in one of SEQ ID NO:1 or SEQ ID NO:3 or SEQ ID NO:5 or SEQ ID NO:7 under low stringency conditions. Preferably, said low stringency is at 42° C.

In another embodiment, the present invention is directed to an isolated nucleic acid molecule encoding bmf or a derivative thereof said nucleic acid molecule selected from the list consisting of:—

(i) a nucleic acid molecule comprising a nucleotide sequence encoding the amino acid sequence set forth in one of SEQ ID NO:2 or SEQ ID NO:4 or SEQ ID NO:6 or SEQ ID NO:8 or a derivative or homolog thereof or having at least about 45% similarity to one or more of SEQ ID NO:2 or SEQ ID NO:4 or SEQ ID NO:6 or SEQ ID NO:8;

(ii) a nucleic acid molecule comprising a nucleotide sequence substantially as set forth in one of SEQ ID NO:1 or SEQ ID NO:3 or SEQ ID NO:5 or SEQ ID NO:7 or a derivative or homolog thereof;

(iii) a nucleic acid molecule capable of hybridizing under low stringency conditions to the nucleotide sequence substantially as set forth in one of SEQ ID NO:1 or SEQ ID NO:3 or SEQ ID NO:5 or SEQ ID NO:7 a derivative or homolog and encoding an amino acid sequence corresponding to an amino acid sequence as set forth in one of SEQ ID NO:2 or SEQ ID NO:4 or SEQ ID NO:6 or SEQ ID NO:8 or a derivative or homolog or a sequence having at least about 45% similarity to one or more of SEQ ID NO:2 or SEQ ID NO:4 or SEQ ID NO:6 or SEQ ID NO:8;

(iv) a nucleic acid molecule capable of hybridizing to the nucleic acid molecule of paragraphs (i) or (iii) under low stringency conditions and encoding an amino acid sequence having at least about 45% similarity to one or more of SEQ ID NO:2 or SEQ ID NO:4 or SEQ ID NO:6 or SEQ ID NO:8; and (v) a derivative or mammalian homolog of the nucleic acid molecule of paragraphs (i) or (ii) or (iii) or (iv).

Reference here to an ability to hybridize to a particular sequence (e.g. SEQ ID NO:1 or SEQ ID NO:3 or SEQ ID NO:5 or SEQ ID NO:7) also includes, in the alternative, an ability to hybridize to its complementary form. In other words, nucleic acid molecules are encompassed which hybridize to SEQ ID NO:1 or SEQ ID NO:3 or SEQ ID NO:5 or SEQ ID NO:7 or their complementary forms.

The nucleic acid molecule may be ligated to an expression vector capable of expression in a prokaryotic cell (e.g. *E. coli*) or a eukaryotic cell (e.g. yeast cells, fungal cells, insect cells, mammalian cells or plant cells). The nucleic acid molecule may be ligated or fused or otherwise associated with a nucleic acid molecule encoding another entity such as, for example, a signal peptide, a cytokine or other member of the Bcl-2 family.

The present invention extends to the promoter for bmf from murine or other mammalian species. Nucleotide sequences comprising the murine and human bmf promoters are shown in SEQ ID NO:9 and SEQ ID NO:10, respectively. The present invention extends to mutants and derivatives of these promoters and their use in genetic constructs, gene therapy and in generating genetically modified animals. A mutant or derivative of a promoter includes one which comprises a nucleotide sequence having at least 70% similarity to SEQ ID NOS:9 or 10 or which is capable of hybridizing to SEQ ID NO:9 or SEQ ID NO:10 or their complementary forms under low stringency conditions.

The present invention extends to the expression product of the nucleic acid molecule hereinbefore defined.

The expression product is Bmf having an amino acid sequence set forth in one of SEQ ID NO:2 or SEQ ID NO:4 or SEQ ID NO:6 or SEQ ID NO:8 or is a derivative or homolog thereof as defined above or is a mammalian homolog having an amino acid sequence of at least about 45% similarity to the amino acid sequence set forth in one of SEQ ID NO:2 or SEQ ID NO:4 or SEQ ID NO:6 or SEQ ID NO:8 or derivative or homolog thereof.

Another aspect of the present invention is directed to an isolated polypeptide selected from the list consisting of:—

(i) a polypeptide having an amino acid sequence substantially as set forth in one of SEQ ID NO:2 or SEQ ID NO:4 or SEQ ID NO:6 or SEQ ID NO:8 or derivative or homolog thereof or a sequence having at least about 45% similarity to one or more of SEQ ID NO:2 or SEQ ID NO:4 or SEQ ID NO:6 or SEQ ID NO:8;

(ii) a polypeptide encoded by a nucleotide sequence substantially as set forth in one of SEQ ID NO:1 or SEQ ID NO:3 or SEQ ID NO:5 or SEQ ID NO:7 or derivative or homolog thereof or a sequence encoding an amino acid sequence having at least about 45% similarity to one or more of SEQ ID NO:2 or SEQ ID NO:4 or SEQ ID NO:6 or SEQ ID NO:8;

(iii) a polypeptide encoded by a nucleic acid molecule capable of hybridizing to the nucleotide sequence as set forth in one of SEQ ID NO:1 or SEQ ID NO:3 or SEQ ID NO:5 or SEQ ID NO:7 or derivative or homolog thereof under low stringency conditions and which encodes an amino acid sequence substantially as set forth in SEQ ID NO:2 or SEQ ID NO:4 or SEQ ID NO:6 or SEQ ID NO:8 or derivative or homolog thereof or an amino acid sequence having at least about 45% similarity to one or more of SEQ ID NO:2 or SEQ ID NO:4 or SEQ ID NO:6 or SEQ ID NO:8;

(iv) a polypeptide as defined in paragraphs (i) or (ii) or (iii) in homodimeric form; and (v) a polypeptide as defined in paragraphs (i) or (ii) or (iii) in heterodimeric form.

As defined earlier, the present invention extends to peptides or derivatives thereof of Bmf. Preferably, said peptide comprises at least S contiguous amino acids of the polypeptide defined in SEQ ID NO:2 or SEQ ID NO:4 or SEQ ID NO:6 or SEQ ID NO:8. The present invention also extends to nucleic acid molecules encoding the peptides of the present invention.

Another aspect of the present invention provides a nucleic acid molecule comprising a nucleotide sequence encoding a polypeptide having one or more of the identifying characteristics of Bmf or a derivative or homolog thereof.

Reference herein to "identifying characteristics" of Bmf includes one or more of the following features:—

(i) a polypeptide which induces apoptosis;

(ii) a polypeptide having an amino acid sequence substantially as set forth in SEQ ID NO:2 or SEQ ID NO:4 or SEQ ID NO:6 or SEQ ID NO:8 or a derivative or homolog thereof;

(iii) a polypeptide having an amino acid sequence of at least 45% similarity to SEQ ID NO:2 or SEQ ID NO:4 or SEQ ID NO:6 or SEQ ID NO:8;

(iv) a polypeptide as defined in paragraph (ii) or (iii) which induces apoptosis;

(v) a polypeptide encoded by a nucleic acid sequence substantially as set forth in SEQ ID NO:1 or SEQ ID NO:3 or SEQ ID NO:5 or SEQ ID NO:7 or derivative or homolog thereof;

(vi) a polypeptide encoded by a nucleic acid molecule capable of hybridizing to the nucleotide sequence as set forth in one of SEQ ID NO:1 or SEQ ID NO:3 or SEQ ID NO:5 or SEQ ID NO:7 under low stringency conditions;

(vii) a polypeptide as defined in paragraph (v) or (vi) which induces apoptosis; and (viii) a non-apoptosis inducing derivative of the polypeptide defined in paragraphs (i) to (vii).

The present invention should be understood to extend to the expression product of the nucleic acid molecule according to this aspect of the present invention.

Although not intending to limit the invention to any one theory or mode of action, the BH3 region is responsible for some of the cytotoxic actions of Bmf. The BH3 region forms an amphipathic α-helix that interacts with the elongated hydrophobic cleft formed by the BH1, BH2 and BH3 regions of pro-survival molecules such as, for example, BCl-x$_L$. The pro-apoptotic action of Bmf reflects its ability to bind to the anti-apoptotic members of the Bcl-2 family.

Still without limiting the invention to any one theory or mode of action, the pro-apoptotic activity of Bmf is thought to be regulated both at the transcriptional level and at the post-translational level. Sequence analysis of the non-coding 5' region of Bmf has revealed a number of putative binding sites for transcription factors such as AP1. Bmf is proposed to interact via a dynein light chain such as DLC2. A dynein light chain is a highly conserved protein which is a component of the myosin V motor complex.

The interaction of Bmf with the myosin V motor complex regulates the pro-apoptotic activity of Bmf. Single or multiple amino acid mutations in Bmf which abolish binding to the dynein light chain are encompassed by the present invention.

Accordingly, a related aspect of the present invention is directed to a variant of an isolated bmf nucleic acid molecule comprising one or more nucleotide mutations in said nucleic acid molecule resulting in at least one amino acid addition, substitution and/or deletion to the polypeptide encoded by said variant wherein said polypeptide cannot bind, couple or otherwise associate with a dynein light chain, such as DLC2.

Preferably, the mutation results in an altered amino acid sequence in the region which binds the dynein light chain. The present invention should be understood to extend to variants of Bmf comprising a mutation resulting in an amino acid addition, substitution and/or deletion in a region functionally equivalent to the regions hereinbefore defined.

Accordingly, the present invention is more particularly directed to a variant of an isolated bmf nucleic acid molecule comprising one or more nucleotide mutations in said nucleic acid molecule resulting in at least one amino acid addition, substitution and/or deletion in the region of the polypeptide encoded by said variant which binds the dynein light chain wherein said polypeptide cannot bind, couple or otherwise associate with a dynein light chain.

Mutations contemplated by the present invention which occur in combination with one or more mutations in another location are also contemplated by the present invention.

The present invention extends to the expression products of the nucleic acid molecule variants defined according to this aspect of the present invention.

Accordingly, the present invention is directed to a variant of an isolated Bmf polypeptide comprising at least one amino acid addition, substitution and/or deletion wherein said polypeptide cannot bind, couple or otherwise associate with the dyncin light chain.

The present invention extends to derivatives of the nucleic acid molecules and polypeptides according to this aspect of the present invention. The term "derivatives" should be understood as previously defined.

As hereinbefore defined, reference to "Bmf" and "bmf" should be understood to include reference to the variant molecules defined according to this aspect of the present invention.

The Bmf of the present invention may be in multimeric form meaning that two or more molecules are associated together. Where the same Bmf molecules are associated together, the complex is a homomultimer. An example of a homomultimer is a homodimer. Where at least one Bmf is associated with at least one non-Bmf molecule, then the complex is a heteromultimer such as a heterodimer. A heteromultimer may include a molecule of another member of the Bcl-2 family or other molecule capable of modulating apoptosis. Furthermore, the present invention contemplates fusion, or hybrids or heteromeric dimers between Bmf and other molecules such as Bim.

The present invention contemplates, therefore, a method for modulating expression of bmf in a mammal, said method comprising administering to said mammal a modulating effective amount of an agent for a time and under conditions sufficient to up-regulate or down-regulate or otherwise modulate expression of bmf. For example, bmf antisense sequences such as oligonucleotides may be introduced into a cell to enhance the ability of that cell to survive. Conversely, a nucleic acid molecule encoding Bmf or a derivative thereof may be introduced to decrease the survival capacity of any cell expressing the endogenous bmf gene. Modulation of the expression of bmf should be understood to extend to modulating transcriptional and translation events such as the splicing pattern of Bmf RNA.

Another aspect of the present invention contemplates a method of modulating activity of Bmf in a mammal, said method comprising administering to said mammal a modulating effective amount of an agent for a time and under conditions sufficient to increase or decrease Bmf activity.

Modulation of said activity by the administration of an agent to a mammal can be achieved by one of several techniques, including but in no way limited to introducing into said mammal a proteinaceous or non-proteinaceous molecule which:
(i) modulates expression of bmf;
(ii) functions as an antagonist of Bmf; and
(iii) functions as an agonist of Bim.

Said proteinaceous molecule may be derived from natural or recombinant sources including fusion proteins or following, for example, natural product screening. Said non-proteinaceous molecule may be, for example, a nucleic acid molecule or may be derived from natural sources, such as for example natural product screening or may be chemically synthesized. The present invention contemplates chemical analogues of Bmf capable of acting as agonists or antagonists of Bmf. Chemical agonists may not necessarily be derived from Bmf but may share certain conformational similarities. Alternatively, chemical agonists may be specifically designed to mimic certain physiochemical properties of Bmf. Antagonists may be any compound capable of blocking, inhibiting or otherwise preventing Bmf from carrying out its normal or pathological biological functions. Antagonists include, but are not limited to parts of Bmf or peptides thereof monoclonal antibodies specific for Bmf or parts of 3 mm, and antisense nucleic acids or oligonucleotides which prevent transcription or translation of bmf genes or mRNA in mammalian cells. Agonists of Bmf and bmf include, for example, the derivative or variant molecules or peptides hereinbefore defined which interact with anti-apoptotic molecules such as Bcl-2, to prevent their functional activity thereby promoting apoptosis. Agonists may also include molecules capable of disrupting or preventing binding of Bmf to the dynein light chain or the interaction of dynein light chain with dynein intermediate chain.

Said proteinaceous or non-proteinaceous molecule may act either directly or indirectly to modulate the expression of bmf or the activity of Bmf. Said molecule acts directly if it associates with Bmf or Bmf to modulate the expression or activity of bmf or Bmf. Said molecule acts indirectly if it associates with a molecule other than bmf or Bmf which other molecule either directly or indirectly modulates the expression or activity of bmf or Bmf.

Accordingly, the method of the present invention encompasses the regulation of bmf or Bmf expression or activity via the induction of a cascade of regulatory steps which lead to the regulation of bmf or Bmf expression or activity.

Increased bmf expression or Bmf activity is useful, for example, for treatment or prophylaxis in conditions such as cancer and deletion of autoreactive lymphocytes in autoimmune disease. Decreased bmf expression or Bmf activity is useful in regulating inhibition or prevention of cell death or degeneration such as under cytotoxic conditions during, for example, γ-irradiation and chemotherapy or during HIV/AIDS or other viral infections, ischaemia or myocardial infarction. Since Bmf is expressed in germ cells, modulating bmf expression or Bmf activity is useful, for example, as a contraceptive or method of sterilisation by preventing generation of fertile sperm.

Another aspect of the present invention contemplates a method of modulating apoptosis in a mammal, said method comprising administering to said mammal an effective amount of an agent for a time and under conditions sufficient to modulate the expression of a nucleotide sequence encoding bmf.

Yet another aspect of the present invention contemplates a method of modulating apoptosis in a mammal, said method comprising administering to said mammal an effective amount of an agent for a time and under conditions sufficient to modulate the activity of Bmf.

Still another aspect of the present invention contemplates a method of modulating apoptosis in a mammal, said method comprising administering to said mammal an effective amount of Bmf or bmf or derivative thereof.

The Bmf, bmf or derivative thereof or agent used may also be linked to a targeting means such as a monoclonal antibody, which provides specific delivery of the Bmf, bmf or agent to the target cells.

In a preferred embodiment of the present invention, the Bmf, bmf or agent used in the method is linked to an antibody specific for said target cells to enable specific delivery to these cells.

Modulation of Bmf or bmf may be accompanied simultaneously or sequentially with the modulation of other molecules or genes such as but not limited to bim or Bim.

Administration of the Bmf, bmf or agent, in the form of a pharmaceutical composition, may be performed by any convenient means. Bmf, bmf or agent of the pharmaceutical composition are contemplated to exhibit therapeutic activity when administered in an amount which depends on the particular case. The variation depends, for example, on the human or animal and the Bmf, bmf or agent chosen. A broad range of doses may be applicable. Considering a patient, for example, from about 0.01 mg to about 10 mg of Bmf or agent may be administered per kilogram of body weight per day. Dosage regimes may be adjusted to provide the optimum therapeutic response. For example, several divided doses may be administered daily, weekly, monthly or other suitable time intervals or the dose may be proportionally reduced as indicated by the exigencies of the situation. The Bmf or agent may be administered in a convenient manner such as by the oral, intravenous (where water soluble), intranasal intraperitoneal, intramuscular, subcutaneous, intradermal or suppository routes or implanting (e.g. using slow release molecules). With particular reference to use of Bmf or agent, these peptides may be administered in the form of pharmaceutically acceptable nontoxic salts, such as acid addition salts or metal complexes, e.g. with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder such as tragacanth, corn starch or gelatin; a disintegrating agent, such as alginic acid; and a lubricant, such as magnesium stearate.

A further aspect of the present invention relates to the use of the invention in relation to mammalian disease conditions. For example, the present invention is particularly applicable to, but in no way limited to, use in therapy or prophylaxis in relation to cancer, degenerative diseases, autoimmune disorders, viral infections or for germ cell regulation.

Accordingly, another aspect of the present invention relates to a method of treating a mammal, said method comprising administering to said mammal an effective amount of an agent for a time and under conditions sufficient to modulate the expression of bmf wherein said modulation results in modulation of apoptosis.

In another aspect, the present invention relates to a method of treating a mammal, said method comprising administering to said mammal an effective amount of an agent for a time and under conditions sufficient to modulate the activity of Bmf wherein said modulation results in modulation of apoptosis.

In another aspect, the present invention relates to a method of treating a mammal said method comprising administering to said mammal an effective amount of Bmf or derivative thereof for a time and under conditions sufficient to modulate apoptosis.

Yet another aspect of the present invention relates to a method of treating a mammal, said method comprising administering to said mammal an effective amount of bmf or derivative thereof for a time and under conditions sufficient to modulate apoptosis.

In yet another aspect, the present invention relates to the use of an agent capable of modulating the expression of bmf or derivative thereof in the manufacture of a medicament for the modulation of apoptosis.

Another aspect of the present invention relates to the use of an agent capable of modulating the expression of Bmf or derivative thereof in the manufacture of a medicament for the modulation of apoptosis.

A further aspect of the present invention relates to the use of Bmf or bmf or derivative thereof in the manufacture of a medicament for the modulation of apoptosis.

Still yet another aspect of the present invention relates to agents for use in modulating bmf expression wherein modulating expression of said bmf modulates apoptosis.

A further aspect of the present invention relates to agents for use in modulating Bmf expression wherein modulating expression of said Bmf modulates apoptosis.

Another aspect of the present invention relates to Bmf or bmf or derivative thereof for use in modulating apoptosis.

In a related aspect of the present invention, the mammal undergoing treatment may be human or an animal in need of therapeutic of prophylactic treatment.

In yet another further aspect, the present invention contemplates a pharmaceutical composition comprising bmf, Bmf or derivative thereof or an agent capable of modulating bmf expression or Bmf activity together with one or more pharmaceutically acceptable carriers and/or diluents. bmf, Bmf or said agent are referred to as the active ingredients.

The pharmaceutical forms suitable for injectable use include sterile aqueous solutions (where water soluble) and sterile powders for the extemporaneous preparation of sterile injectable solutions. It must be stable under the conditions of manufacture and storage and must be preserved against the contaminating action of microorganisms such as bacteria and fungi. The carrier can be a solvent or dilution medium comprising, for example, water, ethanol polyol (for example, glycerol, propylene glycol and liquid polyethylene glycol, and the like), suitable mixtures thereof and vegetable oils. The proper fluidity can be maintained, for example, by the use of surfactants. The preventions of the action of microorganisms can be brought about by various anti-bacterial and anti-fungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with the active ingredient and optionally other active ingredients as required, followed by filtered sterilization or other appropriate means of sterilization. In the case of sterile powders for the preparation of sterile injectable solutions, suitable methods of preparation include vacuum drying and the freeze-drying technique which yield a powder of active ingredient plus any additionally desired ingredient.

When bmf, Bmf and/or Bmf modulators are suitably protected, they may be orally administered, for example, with an inert diluent or with an assimilable edible carrier, or it may be enclosed in hard or soft shell gelatin capsule, or it may be compressed into tablets, or it may be incorporated directly with the food of the diet or administered via breast milk. For oral therapeutic administration, the active ingredient may be incorporated with excipients and used in the form of ingestible tablets, buccal tablets, troches, capsules, elixirs, suspensions, syrups, wafers and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 200 mg of active compound. Alternative dosage amounts include from about 1 µg to about 1000 mg and from about 10 µg to about 500 mg. These dosages may be per individual or per kg body weight. Administration may be per hour, day, week, month or year.

The tablets, troches, pills, capsules, creams and the like may also contain the components as listed hereafter. A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen or cherry flavouring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

Pharmaceutically acceptable carriers and/or diluents include any and all solvents, dispersion media, coatings, antibacterial and anti-fungal agents, isotonic and absorption delaying agents and the like. The use of such media and agents for pharmaceutical active substances is well known in the art and except insofar as any conventional media or agent is incompatible with the active ingredient, their use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 µg to about 2000 mg. Expressed in proportions, the active compound is generally present in from about 0.5 µg to about 2000 mg/ml of carrier. In the case of compositions containing supplementary active ingredients, the dosages are determined by reference to the usual dose and manner of administration of the said ingredients.

The pharmaceutical composition may also comprise genetic molecules such as a vector capable of transfecting target cells where the vector carries a nucleic acid molecule capable of modulating bmf expression or Bmf activity. The vector may, for example, be a viral vector.

Conditions requiring modulation of physiological cell death include enhancing survival of cells utilising, for example, antisense sequence in patients with neurodegenerative diseases, myocardial infarction, muscular degenerative disease, hypoxia, ischaemia, HIV infection or for prolonging the survival of cells being transplanted for treatment of disease. Alternatively, the molecules of the present invention are useful for, for example, reducing the survival capacity of tumour cells or autoreactive lymphocytes. The antisense sequence may also be used for modifying in vitro behaviour of cells, for example, as part of a protocol to develop novel lines from cell types having unidentified growth factor requirements; for facilitating isolation of hybridoma cells producing monoclonal antibodies, as described below; and for enhancing survival of cells from primary explants while they are being genetically modified.

Still another aspect of the present invention is directed to an immunointeractive molecule comprising an antigen binding portion having specificity for Bmf or bmf or derivative thereof.

Reference to "immunointeractive molecule" should be understood as a reference to any molecule comprising an antigen binding portion or a derivative of said molecule. Examples of molecules contemplated by this aspect of the present invention include, but are not limited to, monoclonal and polyclonal antibodies (including synthetic antibodies, hybrid antibodies, humanized antibodies, catalytic antibodies) and T cell antigen receptor binding molecules. Preferably, said immunoreactive molecule is a monoclonal antibody.

According to this preferred embodiment, there is provided a monoclonal antibody having specificity for Bmf or bmf or derivative thereof.

Reference to a molecule "having specificity for Bmf or bmf" should be understood as a reference to a molecule, such as a monoclonal antibody, having specificity for any one or more epitopes of Bmf or bmf. These epitopes may be conformational epitopes, linear epitopes or a combination of conformational and linear epitopes of either the native Bmf or bmf molecule or the denatured molecule.

More preferably, there is provided a monoclonal antibody having specificity for Bmf.

The immunointeractive molecules of the present invention may be naturally occurring, synthetic or recombinantly produced. For example, monoclonal or polyclonal antibodies may be selected from naturally occurring antibodies to Bmf or bmf or may be specifically raised to Bmf or bmf. In the case of the latter, Bmf or bmf may first need to be associated with a carrier molecule. The antibodies and/or recombinant Bmf of the present invention are particularly useful as therapeutic or diagnostic agents. Alternatively, fragments of antibodies may be used such as Fab fragments. Furthermore, the present invention extends to recombinant and synthetic antibodies, to antibody hybrids and to antibodies raised against non-Bmf antigens but which are cross-reactive with any one or more Bmf epitopes. A "synthetic antibody" is considered herein to include fragments and hybrids of antibodies. The antibodies of this aspect of the present invention are particularly useful for immunotherapy and may also be used as a diagnostic tool for assessing apoptosis or monitoring the program of a therapeutic regime.

For example, Bmf and bmf can be used to screen for naturally occurring antibodies to Bmf and bmf, respectively. These may occur, for example in some degenerative disorders.

For example, specific antibodies can be used to screen for Bmf proteins. The latter would be important, for example, as a means for screening for levels of Bmf in a cell extract or other biological fluid or purifying Bmf made by recombinant means from culture supernatant fluid. Techniques for the assays contemplated herein are known in the art and include, for example, sandwich assays, ELISA and flow cytometry.

It is within the scope of this invention to include any second antibodies (monoclonal, polyclonal or fragments of antibodies) directed to the first mentioned antibodies discussed above. Both the first and second antibodies may be used in detection assays or a first antibody may be used with a commercially available anti-immunoglobulin antibody. An antibody as contemplated herein includes any antibody specific to any region of Bmf.

Both polyclonal and monoclonal antibodies are obtainable by immunization with the protein or peptide derivatives and either type is utilizable for immunoassays. The methods of obtaining both types of sera are well known in the art. Polyclonal sera are less preferred but are relatively easily prepared by injection of a suitable laboratory animal with an effective amount of Bmf, or antigenic parts thereof, collecting serum from the animal, and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example, Douillard and Hogan, Basic Facts about Hybridomas, in *Compendium of Immunology* Vol. II, ed. by Schwartz, 1981; Kohler and Milstein, *Nature* 256: 495-499, 1975; Kohler and Milstein, *European Journal of Immunology* 6: 511-519, 1976).

Screening for immunointeractive molecules, such as antibodies, can be a time consuming and labour intensive process. However, the inventors have developed a rapid and efficient flow cytometric screening procedure for the identification of immunointereactive molecules, and in particular antibodies, directed to low abundance cytoplasmic proteins such as, but not limited to, Bmf.

The method according to this aspect of the present invention is based on the analysis of a population of cells, following the incubation of these cells with the antibody of interest together with or separately to a reporter molecule, said population of cells comprising both cells expressing the protein of interest and cells which do not express the protein of interest. This analysis is preferably flow cytometric analysis and the cells expressing the protein of interest are preferably transfected with a nucleic acid molecule encoding the protein of interest to thereby express high levels of said protein. Where the protein is a cytoplasmic protein the cells are permeabalized prior to incubation with the antibody of interest. By screening a population of cells comprising both cells which do not express and cells which do express the protein of interest, determination of which antibodies bind to the protein of interest is simplified since where the subject antibody is directed to the protein of interest, a double fluorescence peak is observed. The lower intensity peak represents background staining while the higher fluorescence intensity peak is the result of specific staining. Where the antibody being screened according to this method is not directed to the protein of interest, a single peak of low fluorescence intensity is observed. Antibodies not specific to the protein of interest but bound to some unknown epitope present in both populations of cells produces a single peak with high fluorescence intensity. This technique provides a rapid and accurate method of screening for immunointeractive molecules directed to low abundance intracytoplasmic molecules (O'Reilly, 1998, supra).

Accordingly, another aspect of the present invention provides a method of detecting an immunointeractive molecule, in a sample, specific for a protein of interest produced by a cell, said method comprising, contacting the sample to be tested with a population of cells comprising a defined ratio of cells producing the protein of interest and cells not producing the protein of interest for a time and under conditions sufficient for immunointeractive molecules, if present in said sample, to interact with said protein of interest and the subjecting said immunointeractive molecule-protein complex to detecting means.

Preferably said immunointeractive molecule is an antibody.

More preferably, said detecting means comprises an anti-immunoglobulin antibody labelled with a reporter molecule capable of giving a detectable signal. Even more preferably said reporter molecule is fluorochrome.

Reference to "sample" should be understood as a reference to any sample potentially comprising an immunointeractive molecule, such as an antibody. Said immunointeractive molecule may be produced by natural, recombinant or synthetic means.

The method of the present invention is predicated on subjecting the cells incubated with the sample of the present invention to flow cytometric analysis to produce a fluorescent signal wherein a differential fluorescent signal is indicative of antibody binding to the target protein expressed by said cells.

The method exemplified herein is directed, but not limited to, screening for immunointeractive molecules comprising an antigen binding site directed to epitopes of Bmf. The promyelomoncytic cell line FDC-P1 is transfected with a Bcl-2 expression construct and an EE (Glu-Glu) epitope-tagged Bmf construct. A 1:1 ratio of Bcl-2 transfected cells to Bmf transfected cells are fixed, permeabilized and contacted with the immunointeractive molecule of interest, such as a hybridoma supernatant. Visualization of antibodies bound intracellular molecules can be achieved via a number of techniques known to those skilled in the art, including, for example, the use of fluorescently labelled reporter molecules. Where the antibody of interest is directed to Bmf, a double fluorescence peak is observed, the lower intensity peak representing background staining of the Bcl-2 transfected negative control cells.

In another aspect of the present invention, the molecules of the present invention are also useful as screening targets for use in applications such as the diagnosis of disorders which are regulated by Bmf. For example, screening for the levels of Bmf or bmf in tissue as an indicator of a predisposition to, or the development or, cancer, a degenerative disease or infertility. The screening of this aspect of the present invention may also be directed to detecting mutations in Bmf or bmf.

Accordingly, another aspect of the present invention contemplates a method for detecting Bmf in a biological sample from a subject, said method comprising contacting said biological sample with an immunointeractive molecule as hereinbefore defined specific for Bmf or its derivatives thereof for a time and under conditions sufficient for an immunointeractive molecule-Bmf complex to form, and then detecting said complex.

Preferably said immunointeractive molecule is an antibody. Even more preferably, said antibody is a monoclonal antibody.

Reference to biological sample according to this aspect of the present invention should be understood as a reference to any sample comprising tissue from a subject, said "tissue" should be understood in its broadest sense to include biological fluid, biopsy samples or any other form of tissue or fluid or extracts therefrom such as DNA or RNA properties.

Still another aspect of the present invention contemplates a method for detecting bmf in a biological sample from a subject, said method comprising contacting said biological sample with an immunointeractive molecule as hereinbefore defined specific for bmf or its derivatives thereof for a time and under conditions sufficient for an immunointeractive molecule-bmf complex to form, and then detecting said complex.

Reference to an "immunointeractive" molecule should be understood as a reference to any molecule which couples, binds or otherwise associates with bmf or Bmf or derivative thereof. For example, said interactive molecule may be a nucleic acid molecule or an anti-nuclear antibody.

The presence of Bmf may be determined in a number of ways such as by Western blotting, ELISA or flow cytometry procedures. Bmf mRNA or DNA may be detected, for example, by in situ hybridization or Northern blotting or Southern blotting. These, of course, include both single-site and two-site or "sandwich" assays of the non-competitive types, as well as in the traditional competitive binding assays. These assays also include direct binding of a labelled antibody to a target.

Sandwich assays are among the most useful and commonly used assays and are favoured for use in the present invention. A number of variations of the sandwich assay technique exist, and all are intended to be encompassed by the present invention. Briefly, in a typical forward assay, an unlabelled antibody is immobilized on a solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent. In accordance with the present invention the sample is one which might contain Bmf including cell extract, tissue biopsy or possibly serum, saliva, mucosal secretions, lymph, tissue fluid and respiratory fluid. The sample is, therefore, generally a biological sample comprising biological fluid but also extends to fermentation fluid and supernatant fluid such as from a cell culture.

In the typical forward sandwich assay, a first antibody having specificity for the Bmf or antigenic parts thereof is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g. from room temperature to about 40° C. such as 25° C.) to allow binding of any subunit present in the antibody. Following the incubation period, the antibody subunit solid phase is washed and dried and incubated with a second antibody specific for a portion of the hapten. The second antibody is linked to a reporter molecule which is used to indicate the binding of the second antibody to the hapten.

An alternative method involves immobilizing the target molecules in the biological sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, β-galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescence and EIA techniques are both very well established in the art and are particularly preferred for the present method. However, other reporter molecules, such as radioisotope, chemiluminescent or bioluminescent molecules, may also be employed.

The present invention also contemplates genetic assays such as involving PCR analysis to detect bmf or its derivatives.

The present invention further provides genetically modified animals in which one or both alleles of bmf are mutated alone or in combination with another mutation in one or both alleles for another Bcl-2 molecule such as but not limited to genes encoding Blk, Bad, Bik, Hrk, Bid, Bim, Noxa, blx3 and/or Puma. The animals may also have mutations in other genes or alleles of genes. Preferably, the genetically modified annals are laboratory test animals such as murine species (e.g. mice, rats), rabbits, guinea pigs or hamsters, livestock animals such as sheep, pigs, horses or cows or non-human mammals such as primates. Conveniently, and preferably, the genetically modified animal is a murine species such as a mouse or rat.

The genetic modification is generally in the form of a mutation such as a single or multiple nucleotide substitution, deletion and/or addition or inversion or insertion. Generally, such a genetically modified animal is referred to as a "knock-out" animal.

Figure 5A:
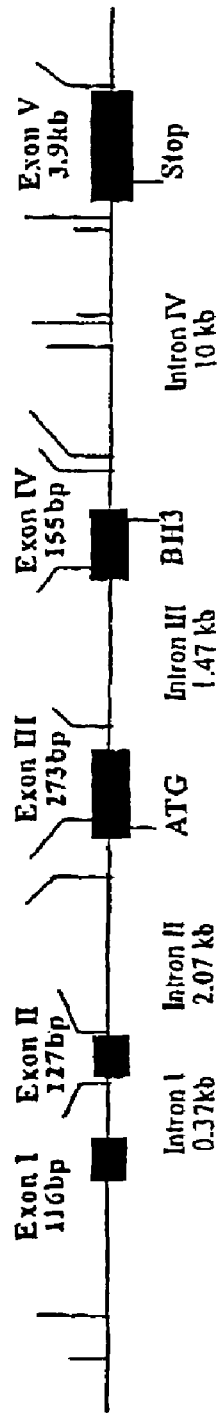
FIG. 5A is a diagrammatic representation showing the genomic organization of the bmf gene locus of the mouse.
Figure 5B:
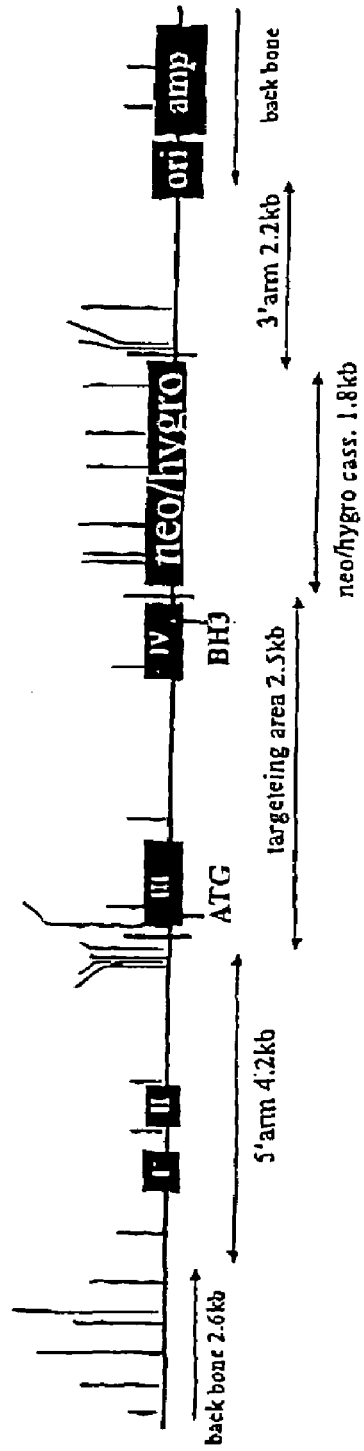
FIG. 5B is a diagrammatic representation of a bmf targeting construct in NFB193neo or NEB193hygro for use in generating knockout mice.

Genetically modified animals and in particular knock-out murine animals may be prepared by any number of means. In one method, a targeting DNA construct is prepared comprising a nucleotide sequence which is sufficiently homologous to a target sequence such a bmf or bim to permit homologous recombination. The bmf or bim targeting sequence may be isogenic or non-isogenic to the target Bmf or Bim sequence. The targeting DNA construct generally comprises a selectable marker within the targeting sequence such that by homologous recombination, the target bmf or bim gene is disrupted by an insertional mutation. The targeting DNA construct is generally introduced into an embryonic stem cell or embryonic stem cell line. One suitable targeting vector is shown in FIG. 5A.

As an alternative to using a selectable marker, a mutation may be introduced which induces a phenotypic change which may then be selected or detected.

Accordingly, another aspect of the present invention provides a method of producing a genetically modified non-human animal, said method comprising introducing into embryonic stem cells of an animal a genetic construct comprising a bmf nucleotide sequence carrying a single or multiple nucleotide substitution, addition and/or deletion or inversion or insertion wherein there is sufficient bmf nucleotide sequences to promote homologous recombination with a bmf gene within the genome of said embryonic stem cells selecting for said homologous recombination and selecting embryonic stem cells which carry a mutated bmf gene and then generating a genetically modified animal from said embryonic stem cell.

Preferably, the genetically modified animal is a murine species such as a mouse or rat.

The Bmf nucleotide sequence may be isogenic or non-isogenic to the bmf gene in the embryonic stem cell.

The term "isogenic" means that the bmf nucleotide sequence in the construct is derived from the same animal strain from which the embryonic stein cell has been derived.

The present invention further contemplates non-homologous-mediated integration of the target DNA sequence.

A range of selectable markers may be employed and reference may be made to U.S. Pat. No. 5,789,215 for general methodologies.

The above method may be similarly adopted for introducing a plurality of mutations into different genes such as, in addition to bmf, other Bcl-2 genes (e.g. those encoding Bim, Blk, Bad, Bid, Hrk, Noxa or Puma) and/or other structural or regulatory genes.

Breeding protocols may also be adopted to introduce mutations or other genetic modifications into Bmf. In one approach, an EMS or other mutagenized mouse is crossed with a non-mutagenized mouse to produce a G1 generation. The G1 generation may then be crossed with an index strain to produce GIFI kindreds which are then screened phenotypically for mutation in bmf. Mutations in bmf may be dominant or recessive and mutations may be detected directly on bmf or by its effect on another gene or on its effect in alleviating the effects of a first mutation on another gene.

All genetically modified animals including knock-out mice carrying mutations in one or both bmf alleles alone or in combination with mutations in other genes such as other Bcl-2 family genes are encompassed by the present invention.

The present invention is further described by the following non-limiting Examples.

EXAMPLE 1

Identification and Cloning of Bmf

The inventors sought novel BH3-only proteins that played a role in embryogenesis. Since Mcl-1-deficient mice have the most severe developmental defect of all knock-out mice lacking pro-survival Bcl-2 family members, Mcl-1 was used as bait. Bmf (Bcl-2 modifying factor) was identified through yeast 2-hybrid screening of a day 17 mouse embryonic library using Mcl-1 as bait. The method used is as follows.

The cDNA libraries from day 17 mouse embryos or from mouse embryos from embryonic day 9 to one day post-partum were prepared in pAD-GAL4-2.1 (HybriZAP-2.1 kit, Stratagene). The bait vector was made by cloning mouse mcl-1 lacking the sequences encoding its hydrophobic C-terminus into pGBT-9 (Clontech). Yeast transformation and plasmid rescue were performed as previously described (Puthalakath et al., 1999, supra). $7 \times 10^5$ clones were screened and one positive clone was obtained. Interaction between Mcl-1 and the novel protein was confirmed by β-galactosidase staining (Puthalakath et al., 1999, supra). Sequence analysis revealed that the clone was a partial one lacking the 5' end. This partial clone was used as the probe to isolate full-length clones by screening a cDNA library derived from the p53$^{-/-}$ KO52DA20 thymoma cell line (Strasser et al., Cell 79: 329, 1994). Human bmf was isolated by screening a human activated T cell cDNA library using mouse bmf as probe. To screen for Bmf-interacting proteins, mouse bmf was subcloned into a pGBT-9 derivative harboring the gene for chloramphenicol acetyltransferase as the selection marker. Out of $5 \times 10^6$ clones screened, 60 positive clones were initially selected, of which 6 were later found to be false positives.

Figure 1D:
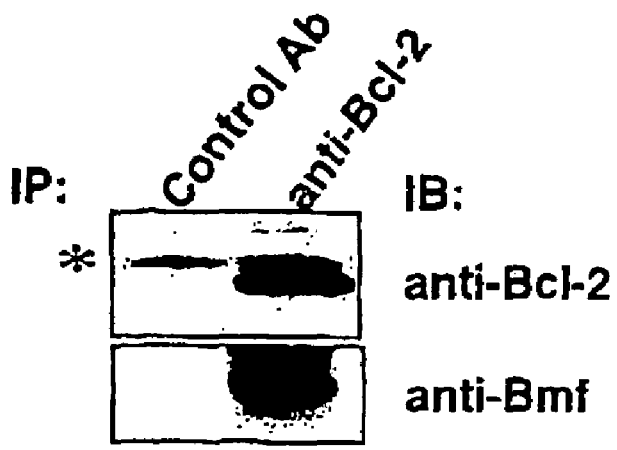

Detailed sequence analysis (Krogh et al., 1994, supra) revealed that Bmf harbors a BH3 domain most similar to that found in Bim, Bik and EGL-1 (FIGS. 1A and B). In the yeast 2-hybrid system, Bmf interacted with Mcl-1 and other pro-survival Bcl-2 proteins (Bcl-2, Bcl-$x_L$ and Bcl-w) but not with the pro-apoptotic family members tested (Bax, Bid and Bad). When transiently overexpressed in 293T cells, Bmf could be co-immunoprecipitated with pro-survival Bcl-2 family members Bcl-2 and Bcl-w (FIG. 1C), as well as BCl-$x_L$ and Mcl-1, but did not bind pro-apoptotic Bax or the BH3-only protein Bim. The interaction of Bmf with Bcl-2 or Bcl-w was greatly diminished by mutating the invariant leucine (L13SA) within its BH3 domain (FIG. 1C). Furthermore, mutations of conserved residues within the BH1 (G145B) or BH2 (W188A) domain of Bcl-2, which abolish its binding to Bim (O'Connor et al., EMBO J. 17: 384, 1998) or Bax (Yin et al., Nature 369: 321, 1994), also disrupt its binding to Bmf. Significantly, endogenous Bmf could be co-immunoprecipitated with endogenous Bcl-2 from detergent lysed MCF-7 human breast carcinoma cells (FIG. 1D), excluding the possibility that these proteins associate only when overexpressed.

Figure 1E:
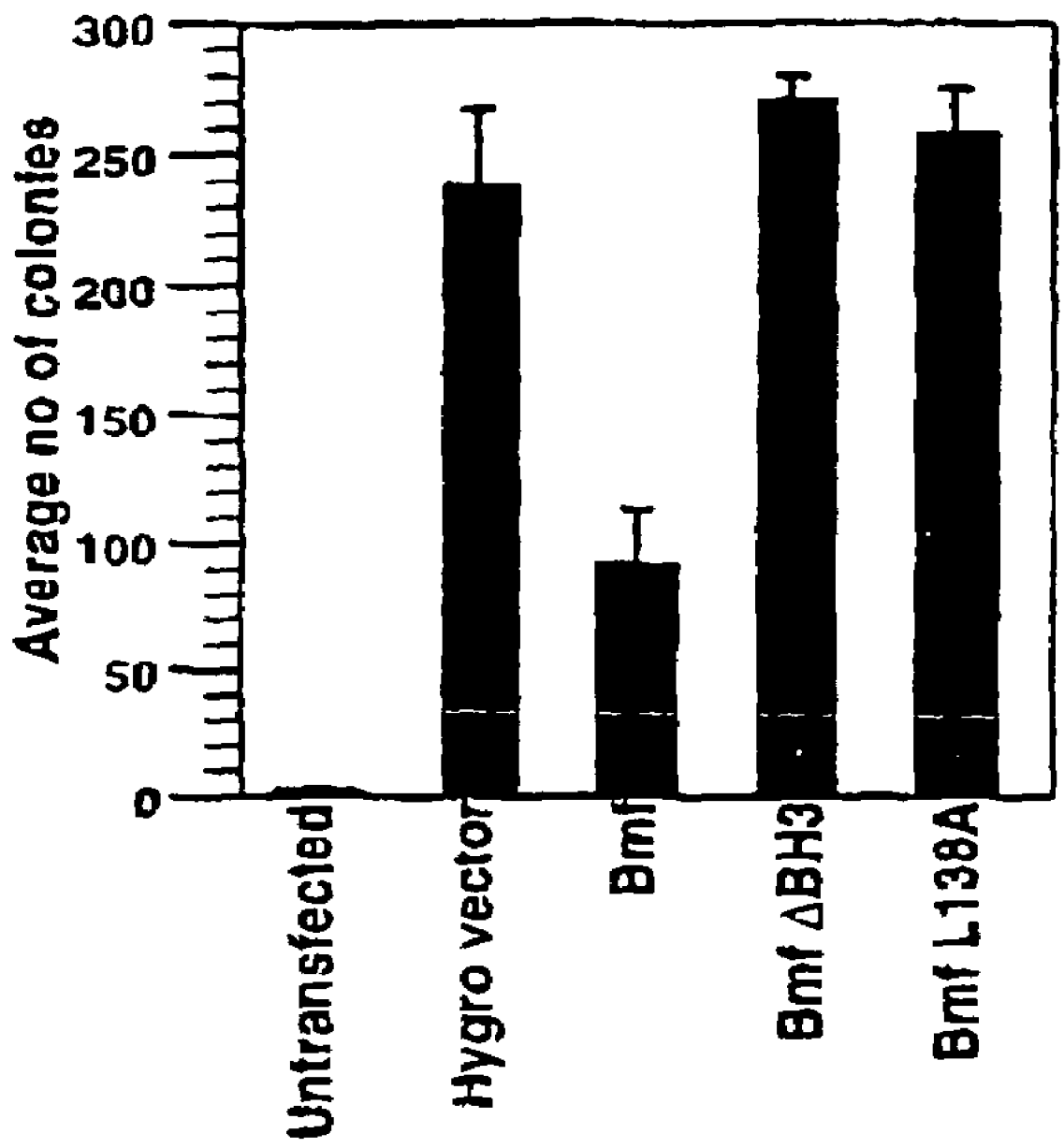
Figure 2A:
FIG. 2 is a representation showing Bmf is regulated by interaction with DLC2. (A) Expression of bmf mRNA in thymocytes treated with various apoptotic stimuli. Total RNA was isolated from thymocytes (freshly isolated) or at the indicated time points after culture in the absence of cytokines or treatment with dexamethasone (1 µM), γ-radiation (10 Gy) or ionomycin (1 µg/mL). These conditions all induce substantial apoptosis and, hence, no RNA could be harvested after 7 hours of treatment. Then 2 µg RNA was reverse transcribed using AMV reverse transcriptase. Five fold dilutions of the cDNA were subjected to PCP analysis using bmf specific primers. After transfer of the PCR products, nitrocellulose filters were probed with a $^{32}$P-labeled internal bmf oligonucleotide probe. (B) Bmf binds to DLC2 through its dynein light chain binding region. Co-immunoprecipitation experiments were performed as described in the legend to FIG. 1C, from lysates of 293T cells transiently expressing FLAG-tagged DLC2 and EE-tagged wt Bmf; a B3H3 mutant (L138A) of Bmf or DLC binding region mutants of Bmf (A69P or AAA), Bid or Bax. The asterisk (*) indicates the light chain of the mAb used for immunoprecipitation (C) Interaction with DLC2 regulates the pro-apoptotic potency of Bmf. FDC-P1 cells stably expressing Bcl-2 plus EE-tagged wt Bmf, a BH3 mutant (L138A) of Bmf or DLC binding region mutants of Bmf (A69P or AAA) were deprived of IL-3 for 1-6 days. Cell viability was assessed by propidium iodide staining and flow cytometric analysis. Values are means (+/− SD) of three independent experiments done with four independent clones of each genotype.
Figure 2B:
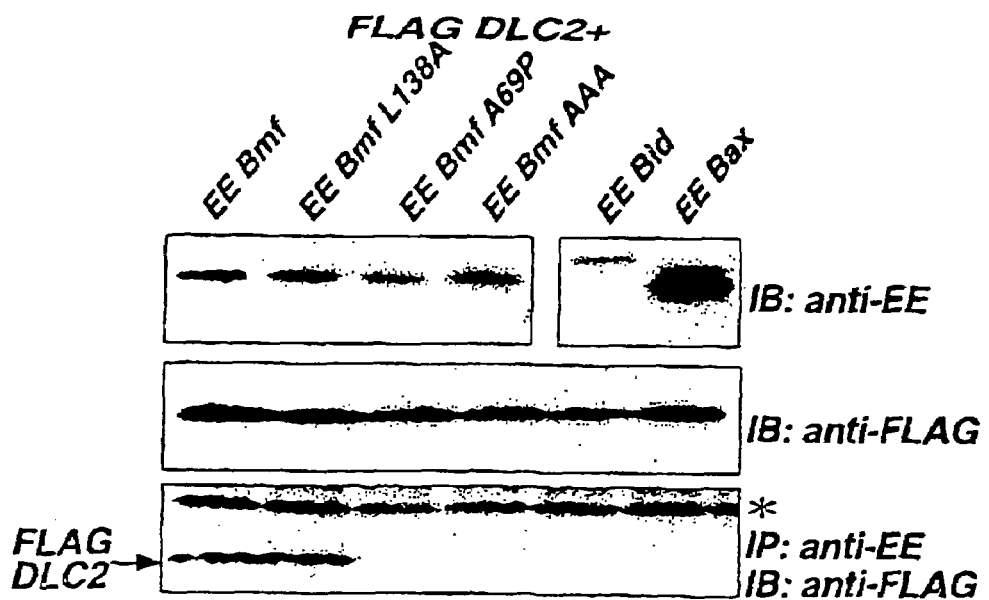
Figure 2C:
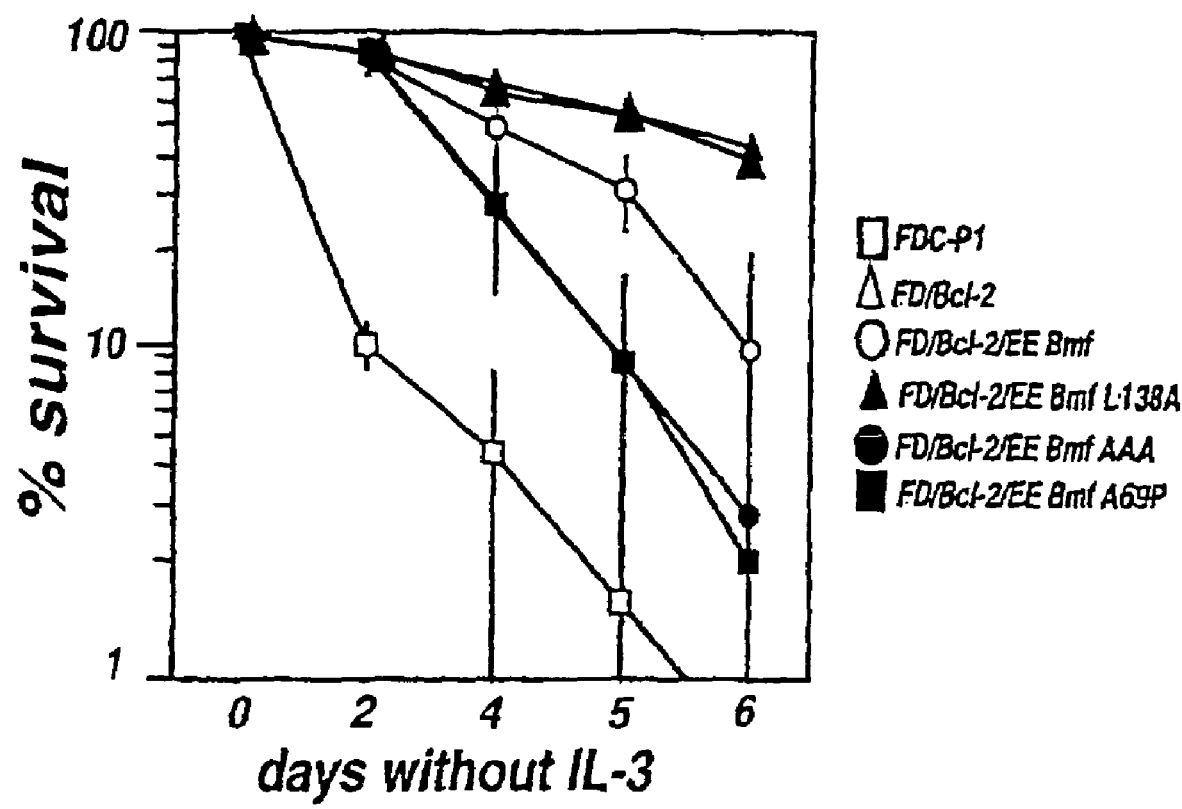

The biological activity of Bmf was investigated by transiently overexpressing it in Jurkat human T lymphoma cells, as well as in stably transfected L929 mouse fibroblasts (FIG. 1E) or in IL-3-dependent FDC-P1 mouse promyelocytic cells (FIG. 2C). Expression of Bmf triggered apoptosis in ~80% of Jurkat cells within 24 hours and reduced formation of L929 fibroblast colonies by about 65% (FIG. 1E). Bmf-induced apoptosis in Jurkat cells could be blocked by the caspase inhibitor baculovirus p35, or by co-expression of Bcl-2 or its homologs (Bcl-$x_L$, Bcl-w, Mcl-1) but not by BH1 (G145E) or BH2 (W188A) domain mutants of Bcl-2. Consistent with its pro-apoptotic activity, high levels of Bmf could be expressed stably in FDC-P1 cells only when Bcl-2 (or one of its homologs) was also expressed. Such Bmf/Bcl-2 co-expressing FDC-P1 cells died more rapidly than Bcl-2 expressing cells in response to cytokine withdrawal (FIG. 2C), γ-irradiation or treatment with etoposide. In all the cell death assays performed, Bmf mutants that lack the BH3 domain or have the L138A mutation in it were inert (FIGS. 1E and 2C). These results establish that Bmf is a BH3-only protein that binds pro-survival Bcl-2 family members to initiate apoptosis.

EXAMPLE 2

Expression Patterns of Bmf

Figure 1F:
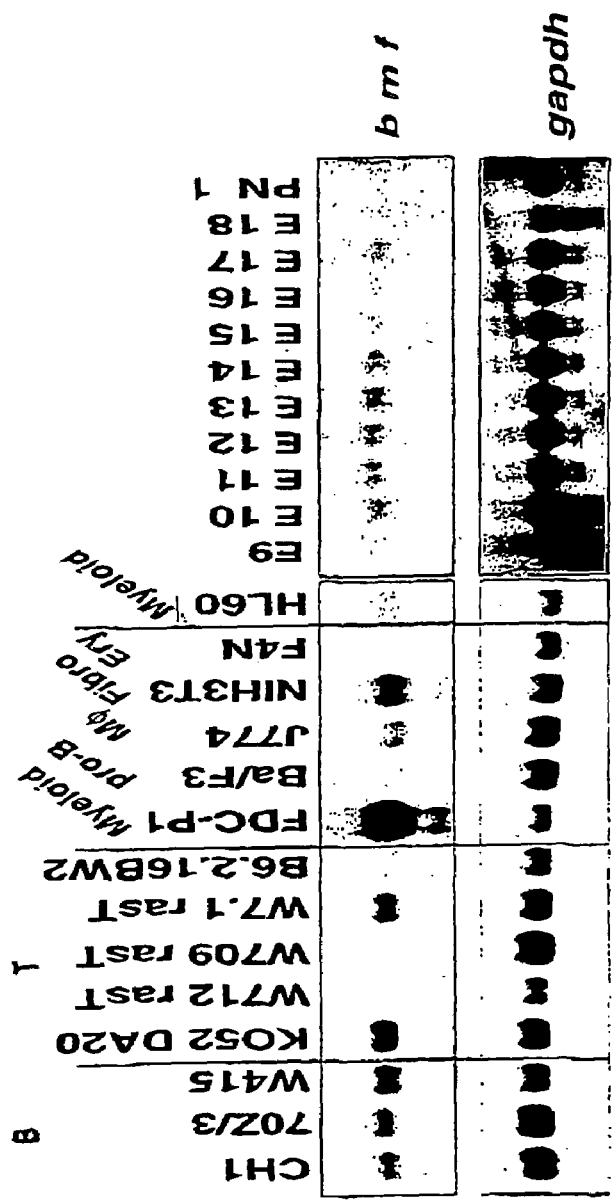
Figure 1G:
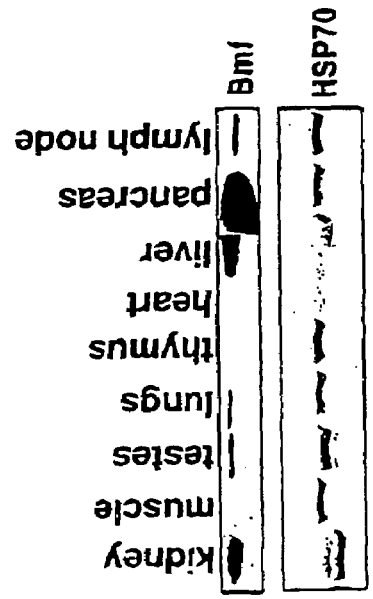

The expression pattern of Bmf was investigated by Northern blotting, RT-PCR and Western blotting. bmf mRNA was found in many cell lines of B and T lymphoid, myeloid or fibroblastoid origin and in mouse embryos at all developmental stages from E9 to birth (FIG. 1F). Western blotting of cell lysates using affinity purified rabbit polyclonal antibodies or rat monoclonal antibodies (described below) detected a single band corresponding to Bmf in many organs, with prominent levels found in pancreas, liver, kidney and hematopoietic tissues (FIG. 1G). Thus, Bmf is expressed during embryogenesis and in many adult tissues.

Monoclonal rat antibodies to dynein light chains and Bmf were generated using a previously published protocol (O'Reilly et al., 1998, supra). In brief, Wistar rats were immunized with purified recombinant mouse DLC1/LCS or mouse Bmf. Spleen cells from immunized rats were fused with Sp2/0 myeloma cells. The resulting hybridoma clones were screened for production of specific antibodies by immunofluorescent staining and flow cytometric analyses. Hybridomas were cloned twice and antibodies were purified either on a protein-G column (Amersham Pharmacia) or on a sepharose column conjugated with MAR 18.5 (monoclonal mouse anti-rat Igκ) antibodies. Monoclonal antibody 11F7 (rat IgG 2a/κ) recognizes mouse and human DLC1/LC8 and DLC2 whereas 10D6 (rat μ/κ) detects mouse and human DLC1/LC8 but not DLC2. Monoclonal antibodies 9G10 and 12E10 (both rat γ2a/κ) detect endogenous mouse and human Bmf by Western blotting and immunoprecipitation. To generate polyclonal anti-Bmf antibodies, New Zealand White rabbits were immunized with 500 μg of recombinant mouse Bmf. Booster immunisations were given at intervals of three weeks. Serum was collected after 12 days and purified over a sepharose column conjugated with recombinant mouse Bmf protein.

EXAMPLE 3

Apoptotic Structure

To assess whether bmf expression was induced by apoptotic stimuli, RT-PCR analyses were performed of mRNA from thymocytes exposed to various forms of stress, including cytokine deprivation, γ-irradiation or treatment with dexamethasone or ionomycin (described below). None of these stimuli had any impact on bmf expression (FIG. 2A), prompting the inventors to investigate whether Bmf is regulated post-translationally, perhaps by interacting with other proteins. A yeast 2-hybrid screen of a mouse embryo cDNA library with Bmf as bait isolated 14 independent clones of Mcl-1 and, surprisingly, more than 40 clones encoding dynein light chain (DLC). In a previous screen, Bim had isolated exclusively DLC1/LC8 (Puthalakath et al., 1999, supra). In contrast, most dynein light chain clones interacting with Bmf encoded the closely related protein DLC2 (Naisbitt et al., *J. Neurosci.* 20: 4524, 2000). Co-immunoprecipitation experiments in transiently transfected 293T cells confirmed the interaction of Bmf with DLC2 (FIG. 2B). Sequence comparison revealed that Bmf has, in addition to the BH3 domain, a short region (aa67-DKATQTLSP) that closely resembles one in Bim (aa51-DKSTQTPSP) that mediates its binding to DLC1/LC8 (FIG. 1A). This is the DLC-binding motif of Bmf, because mutations within it (A69P or D67K68A69>AAA, hereafter referred to as AAA mutation) abrogated the interaction of Bmf with DLC2 in yeast and in mammalian cells (FIG. 2B). Moreover, upon IL-3 deprivation or γ-irradiation, FDC-P1 cells co-expressing Bcl-2 and non-DLC2-binding mutants of Bmf died much more rapidly than those co-expressing Bcl-2 and wild-type Bmf FIG. 2C). These Bmf mutants also suppressed the formation of L929 fibroblast colonies more potently than wild-type Bmf. Hence, interaction with DLC2 negatively regulates the pro-apoptotic activity of Bmf.

RT-PCR analysis of bmf mRNA expression was performed using the following primers: 5' (sense) primer 5'CCGGATG-GATCACCAGGAATG3' [SEQ ID NO:11], 3' (antisense) primer 5'CAGAGCTGACAAAGGCACAG3' [SEQ ID NO:12]. Detection of the PCR products on Southern blots was performed using the internal bmf primer 5'CCACTTC-CTGGAGAACATCA3' [SEQ ID NO:13]. For analysis of GAPDH expression, the following primers were used: 5' (sense) primer 5'TGATGACATCAAGAAGGTGGT-GAAG3' [SEQ ID NO:14], 3' (antisense) primer 5'TCCTTG-GAGGCCATGTAGGCCAT3' [SEQ ID NO:15] and the internal primer 5'CCCGGCATCGAAGGTGGAAGAG3' [SEQ ID NO:16].

EXAMPLE 4

Functional Model

Figure 3A:
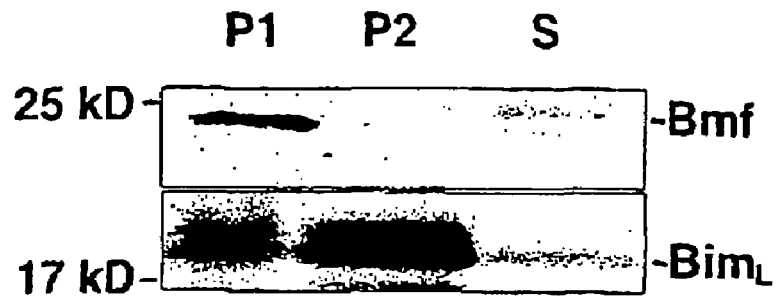
FIG. 3 is a photographic representation showing that Bmf associates with the actin-based myosin V motor complex through DLC2. (A) Lysates from 10$^7$ MCF-7 cells were separated into P1, P2 and S fractions. Proteins from each fraction were then size-fractionated by SDS-PAGE, transferred onto nitrocellulose and probed with mAbs specific to Bmf, Bim$_L$ (O'Reilly et al., *Biotechniques* 25: 824, 1998), myosin V (Espreafico et al., *J. Cell Biol.* 119: 1541, 1992) or dynein intermediate chain IC74 (Sigma). (B) MCF-7 cells were treated for 3 hours with either cytochalasin D (10 µM) or toxin B (10 ng/mL), then fractionated and processed as described under (A). (C) Characterization of novel mAbs that recognize both DLC1/LC8 and DLC2, or just DLC1/LC8. Extracts from 293T cells transiently expressing FLAG-tagged DLC1 or DLC2 were run on SDS-PAGE gels, electroblotted onto nitrocellulose membranes and probed with rat monoclonal antibodies 11F7 (which recognizes both DLC1 and DLC2) or 10D6 (which recognizes only DLC1). The faint bands of lower molecular weight marked by arrows indicate endogenous DLC1. (D) Myosin V is associated mostly with DLC2 whereas dynein predominantly associates with DLC1/LC8. Cytoplasmic dynein was enriched from MCF-7 cells (Paschal et al., *Methods Enzymol.* 196: 181, 1991) and myosin V was purified from mouse spleen (m) or chicken brain (c) (Cheney, *Methods Enzymol.* 298: 3, 1998). These enriched fractions were analyzed by Western blotting using rat mAbs 11F7 (recognizes DLC1/LC8 and DLC2) or 10D6 (recognizes-only DLC1/LCS). Nitrocellulose membranes were probed with antibodies to myosin V or IC74 (Sigma) to demonstrate purity of the myosin and dynein motor fractions. (E) Extracts from mouse spleen cells (200 µg protein) were incubated for 3 hours at 4° C. with recombinant GST or GST-tagged FADD, Bmf or Bim$_L$ proteins, and the bound proteins recovered on glutathione sepharose beads. Bound proteins were eluted from the beads by boiling in Laemmli buffer (non-reducing), size-fractionated by SDS-PAGE and electro-blotted onto nitrocellulose membranes, which were probed with an antibody to myosin V (Espreafico et al., 1992, supra). The nitrocellulose membrane was stained with amido black (bottom panel) to document that comparable amounts of proteins were used in the pull down experiments. (F) Lysates from 10$^7$ MCF-7 cells were fractionated through a 5-20% w/v sucrose gradient. The pellet and soluble fractions were analyzed by Western blotting for the presence of Bmf, Bim, DLC1/LC8 or DLC2.
Figure 3B:
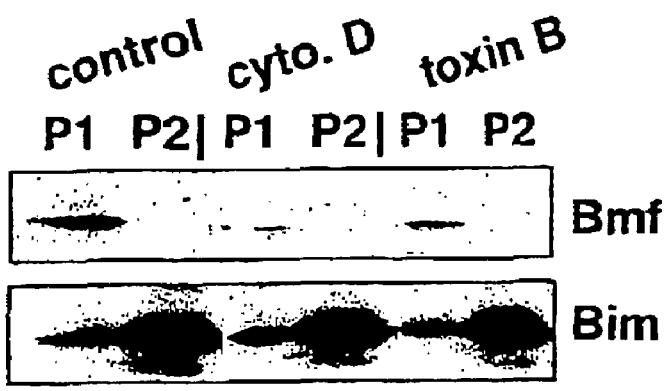

The question considered by the inventors is why Bmf is controlled by binding to highly related partners, DLC-1 or DLC-2. It is proposed that Bmf is sequestered to sites within the cell in order to sense distinct stress stimuli. Separation of cellular proteins into the filamentous actin and the paclitaxel (taxol)-polymerizable microtubular fractions revealed that, consistent with previous results (Puthalakath et al., 1999, supra), Bim and dynein intermediate chain (IC74) largely co-migrated with microtubular components (P2), whereas Bmf and myosin V were confined to the filamentous actin-containing P1 fraction (FIG. 3A). Furthermore, treating cells with actin depolymerizing agents, such as cytochalasin D or *C. difficcili* toxin B, released Bmf from the filamentous actin-containing P1 fraction whereas the fractionation of Bim was unaffected (FIG. 3B).

For subcellular fractionation, $5 \times 10^6$ MCF-7 cells were lysed in 500 μL extraction buffer containing 1% Triton-X-100. Cell debris and nuclei were removed by centrifugation at 2000 g. The supernatant was then incubated for 13 minutes at 37° C. with 100 μM paclitaxel (taxol) and S units of apyrase (Sigma). This mixture was then loaded on top of a 0.5 mL cushion of 7.5% sucrose (made in the extraction buffer) and centrifuged at 140,000 g for 30 minutes at 30° C. The pellet was saved as the microtubular P2 fraction and the supernatant as the S fraction. To obtain the actin-enriched P1 fraction without contamination by microtubular constituents, MCF-7 cells were cultured for 2 hrs in the presence of 2 μg/mL colchicine and 1 μg/mL nocodazole prior to lysis. These lysates were then cleared of cell debris and nuclei (described above) and subsequently centrifuged for 60 minutes at 4° C. at 140,000 g to obtain the pellet (P1) fraction. For fractionation of extracts on sucrose gradients, $10^7$ cells were lysed in 500 μL extraction buffer. After removing cellular debris and nuclei, the supernatants were treated with 100 μM paclitaxel (taxol) plus 5 units of apyrase and incubated at 37° C. for 13 minutes before loading onto a 5-20% sucrose gradient (prepared in extraction buffer containing 1% Triton X-100) and centrifuging for 18 hours at 15° C. at 140,000 g.

Figure 3C:
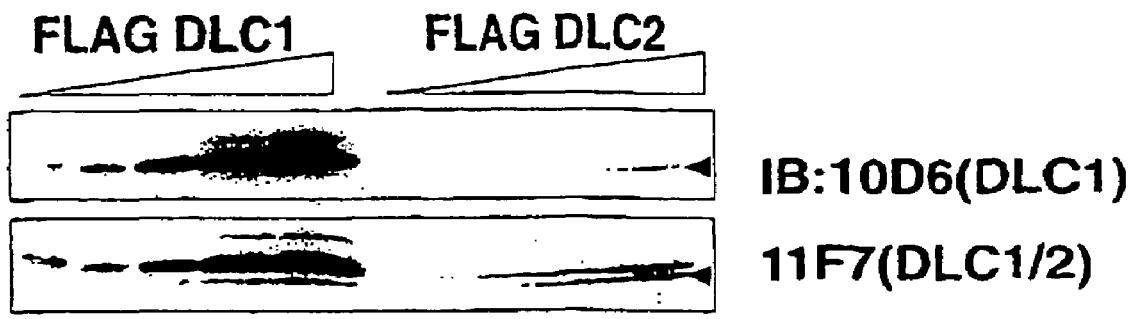

The distinct localization of Bmf and Bim may be determined largely by their preferred dynein light chain partners. Contrary to a previous report (Benashski et al., *J. Biol. Chem.* 272: 20929, 1997), by using monoclonal antibodies that either recognize only DLC1/LC8 or both DLC1/LCS and DLC2 (FIG. 3C), the inventors showed that purified myosin V motor complexes contained DLC2 but not DLC1/LC8 (FIG. 3D). This observation indicated that Bmf, by being preferentially bound to DLC2, might be complexed with myosin V on filamentous actin rather than forming part of the dynein motor complex. Consistent with this notion, incubation of extracts from mouse spleen cells with recombinant Bmf and Bim confirmed that only Bmf associated with myosin V (FIG. 3B). Furthermore, Bmf and Bim showed distinct migration patterns after subcellular fractionation of lysates from MCF-7 cells on sucrose gradients (FIG. 3F). Since DLC1/LC8 forms homodimers avidly and since it binds Bim and IC74 through the same region (Lo et al., *J. Biol. Chem.* 276: 14059, 2001), one partner of a DLC1/LC8 homodimer probably interacts with IC74 whilst the other binds Bim, thereby sequestering it to the microtubular dynein motor complex. It is likely that DLC2 homodimers sequester Bmf to filamentous actin by binding with one arm to Bmf and with the other to myosin V.

Figure 4A:
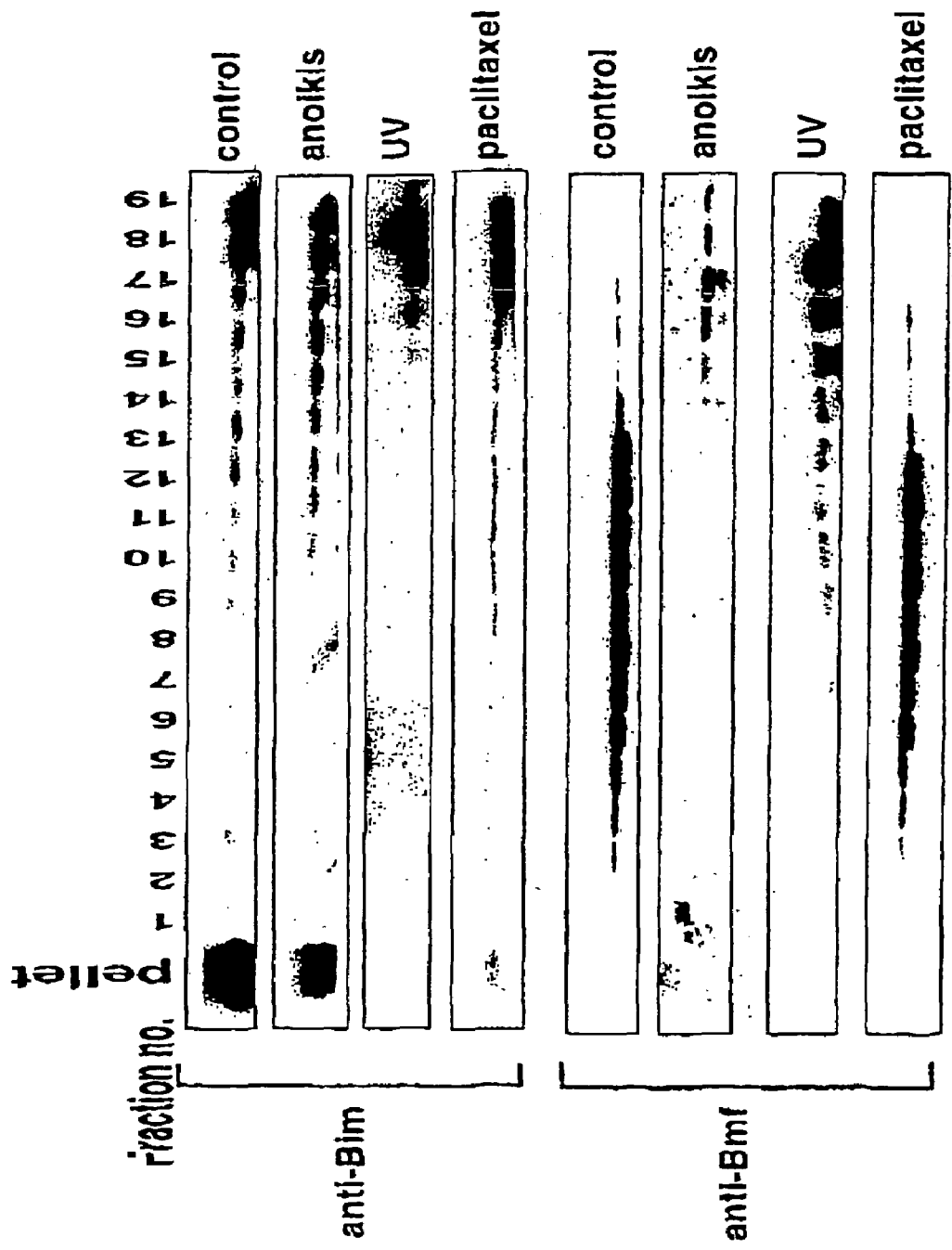
FIG. 4 is a photographic representation showing that Bmf and Bim are released from their sequestration sites in response to distinct apoptotic stimuli. (A) MCF-7 cells were cultured in the presence of the broad-spectrum caspase inhibitor zVAD-fmk (50 µM). Lysates from control (untreated) cells were compared with those from cells subjected to various apoptotic stimuli, including anoikis (culturing cells for 24 hours in suspension on poly-hema coated bacterial Petri dishes), UV-irradiation (100 J/m$^2$), paclitaxel (taxol 1 µM). Lysates of 10$^7$ cells were fractionated through sucrose gradients. The pellet and soluble fractions were collected and analyzed by Western blotting for Bmf and Bim using specific monoclonal antibodies. (B) During anoikis, Bmf translocates to mitochondria and binds to Bcl-2. Mitochondria were purified as previously described from 2×10$^8$ healthy MCF-7 cells or cells subjected to anoikis. Mitochondrial proteins were extracted in lysis buffer containing 1% v/v Triton X-100 (Puthalakath et al., 1999, era). Immunoprecipitations were performed with anti-human Bcl-2 mAb (Bcl 2-100) bound to sepharose beads. Bound proteins were eluted by boiling the beads in Laemmli buffer (non-reducing), size-fractionated by SDS-PAGE, electroblotted onto nitrocellulose membranes and probed with mAbs to Bcl-2, Bmf or dynein light chains.
Figure 4B:
Figure 4B:
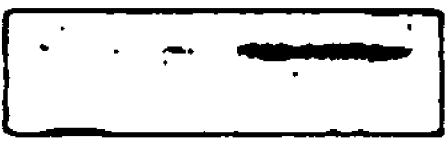
Figure 4B:
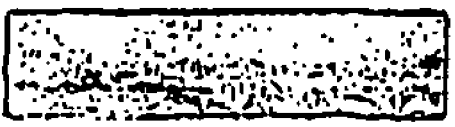
Figure 4B:

The inventors next investigated whether Bmf and Bim are activated by distinct apoptotic stimuli using cells that express both proteins endogenously. Consistent with our previous results (Puthalakath et al., 1999, supra), UV-irradiation of MCF-7 cells released Bim from the pellet fraction where the dynein motor complex resided. When lysates of healthy or damaged MCF-7 cells were compared by sucrose gradient centrifugation, it became apparent that Bmf also translocated from denser to lighter fractions in response to UV-irradiation (FIG. 4A). Treatment with paclitaxel (taxol), a chemotherapeutic drug known to polymerize microtubules, released Bim but not Bmf (FIG. 4A). Consistent with a critical role for Bim in this pathway to apoptosis, Bim-deficient thymocytes are abnormally resistant to the cytotoxic effects of paclitaxel (Frisch and Ruoslahti, *Science* 286(5445): 1735-1738, 1999). On the other hand, anoikis (absence of cell attachment and integrin signaling), an apoptotic stimulus that affects the actin cytoskeleton (Frisch and Ruoslahti, 1997, supra), resulted in the selective release of Bmf but not Bim (FIG. 4A). Since these experiments were conducted in the presence of the broad-spectrum caspase inhibitor zVAD-fmk at a concentration (50 µM) sufficient to block caspase activation, the release of Bmf and/or Bim are likely to represent initiating events in apoptosis signaling rather than being a consequence of apoptotic changes. Importantly, the inventors showed that endogenous Bmf (together with DLC2) released during anoikis could be co-immunoprecipitated with endogenous Bcl-2 isolated from mitochondria (FIG. 4B). In contrast, negligible Bmf was found complexed with Bcl-2 isolated from mitochondria of healthy cells.

Collectively, the inventors' data demonstrate that Bmf and Bim represent two pro-apoptotic BH3-only proteins that transduce distinct death signals caused by different forms of cell stress. They seem to represent sentinels mounted on the main cytoskeletal structures to monitor the well-being of the cell. For example, disturbance of the microtubules by paclitaxel activates Bim but not Bmf, whereas anoikis, which affects the actin cytoskeleton, activates Bmf but not Bim. Since deregulated expression of anti-apoptotic Bcl-2 can promote tumorigenesis (Strasser et al., *Nature* 348: 331, 1990), it is possible that abnormalities in pro-apoptotic BH3-only proteins can also cause cancer. The gene for human bmf is located on chromosome 15q14, identified as the site of a candidate tumor suppressor gene lost in many metastastic but not primary carcinomas (Wick et al., *Oncogene* 12: 973, 1996). Anoikis has been implicated as a barrier against metastatic tumor growth (Ruoslahti and Reed, *Cell* 77: 477, 1994). Metastatic tumors harboring 15q14 mutations may, therefore, have abnormalities in their expression or function of Bmf.

EXAMPLE 5

Generation of Bmf Knock-out Mice

Mice are selected with a C57BL/6 background which are back crossed into C57BL/6. Offspring are genotyped using PCR using primers specific for wild-type or mutant bmf genes.

A bmf targeting vector is generated as shown in FIG. 5A. A neomycin or hygromycin sequence is used as the selectable marker. The construct is introduced into embryonic stem cells and transformed cells selected using neomycin or hygromycin. The transformed embryonic stem cells are then used to generate genetically modified mice.

EXAMPLE 6

Genomic Organization of Bmf and Identification of Promoter Regions

The genomic organization of the murine bmf gene is shown in FIG. 5A. Upstream of this region comprises a promoter region as outlined in SEQ ID NO:9. A corresponding promoter from the human bmf gene is outlined in SEQ ID NO:10.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The invention claimed is:

1. An isolated nucleic acid molecule encoding a Bcl-2 modifying factor (Bmf) wherein said nucleic acid molecule comprises the nucleotide sequence as set forth in SEQ ID NO: 3.

2. An isolated nucleic acid molecule encoding a Bmf wherein said nucleic acid molecule consists of the nucleotide sequence as set forth in SEQ ID NO: 3.

3. An isolated variant nucleic acid molecule encoding a mutant Bcl-2 modifying factor (Bmf) wherein said variant nucleic acid molecule comprises a variation of the nucleotide sequence as set forth in SEQ ID NO: 3 wherein the variation encodes a Bmf mutation selected from the group consisting of L138A, A69P, and the double mutation D67A and K68A, and wherein said mutant Bmf containing the L138A mutation has diminished binding to a member of the pro-survival Bcl-2 family selected from the group consisting of Bcl-2, Bcl-$x_L$, Bcl-w, and Mcl-1, compared to Bmf encoded by the nucleotide sequence as set forth in SEQ ID NO: 3, and said mutant Bmf containing the A69P mutation or the D67A, K68A double mutation binds a member of the pro-survival Bcl-2 family selected from the group consisting of Bcl-2, Bcl-$x_L$, Bcl-w, and Mcl-1.

4. A variant of the nucleic acid molecule of claim 3, wherein said variant encodes a Bmf mutant which contains the mutation L138A.

5. A variant of the nucleic acid molecule of claim 3, wherein said variant encodes a Bmf mutant which contains the mutation A69P.

6. A variant of the nucleic acid molecule of claim 3, wherein said variant encodes a Bmf mutant which contains the double mutation D67A and K68A.

* * * * *

SEQUENCE LISTING

```
<160> NUMBER OF SEQ ID NOS: 27

<210> SEQ ID NO 1
<211> LENGTH: 4688
<212> TYPE: DNA
<213> ORGANISM: mouse

<400> SEQUENCE: 1
cggcacgagc ggagcgggcg tattttggaa acaataccgc gcggtgtgcc gtggcctcct      60
cccgcgccag ctcgcgcctg cagcagtcgc tgccgcagcc cgcgccaccg cctcccaccg     120
cagcccgctg gagtttgccc ccttcttccc aatcgagtgt gggcaccaag cccccgagt     180
```

```
gttcttcacc ctggaccctg gcgcagagcc ctggcatcac aactcggagg ctgagacgct    240
gtcctggagt cacccaggag agatggagcc acctcagtgt gtggaggagc tagaagatga    300
tgtgttccag tcagaggatg gggagccagg acacagcct gggggcttgc tctctgctga     360
cctgtttgcc cagagccagc tggactgtcc cctcagtcga ctccagctct ccctctcac    420 ccactgctgt ggtccggac tccggcccat aagccaggaa acaaggcca ctcagaccct      480 cagtccagct tccccaagcc agggtgtcat gctgccttgt ggggtgacag aggaacccca   540
gagactcttt tacggcaacg ctggctacag gcttcctctc cctgccagtt ccctgcagg    600 ctcaccccct ggggagcagc ccctgaagg acagttcctt cagcaccgag cagaggtgca    660
gatcgccaga aagcttcagt gtattgcaga ccagttccat cggcttcata cgcaacaaca    720
ccagcagaac cgagaccgtg cgtggtggca ggtcttcctc ttccttcaaa acctcgccct    780
gaacagacaa gaaaacaggg aagggtggg gccctggtga ggctggaccg ccctggccgg     840
atggatcacc aggaatgcag tctgggagga cagatactgt cttgttaagt tttgttatcc   900
gtaactttct atccatgtgt acatattaca tgccccagtg ggatcttctt tccccgttca   960
gaacctccac tgaggatggg ggcctttgtc aaacactgtt gaaggagagg cagctgtgtc   1020
tgctggtaga gttcctaagg ctctgaagat gaccagttgg tgatgttctc caggaagtgg   1080
actgagactt gctaccggag ctggttaagt caggttaggc tcccagtacc atcaaacatg   1140
tcagccttcc ttcgtgcctg atggatcatg gctttaaccc accaggaccc tgtctgggag   1200
cctcctggct aagatcaact gtgccttggc tagcccgatt cacgtctggg ttcccacttg   1260
gcacagccag cgcccaccgc atgggctcag ggattcttac tcagacgctg tcaacttccg   1320
gaagacctca ggggggtcg gacttctcca agaacccctc aaatttgcca caaatgaat    1380 caaacttgag aggcttcaag tctgactcgg tcctacatgg aagcccttg attggtcccc    1440 aagggtgcaa actactgcca cctttgctgg agccaagtag ccagtcacca tgccgttgta   1500
cccagcggcc tgtgcctttg tcagctctgt tttcagaaga ccctgccaat gactggactg   1560
gatctgtctg catccatctc agcagaagca cttggagatg gggtgggctt gctggggcg   1620 tgggaaccca gcagccatcc cactgataag ttggtcccgg gggaatccta gacctcttgg   1680
tttccttgga aacgtgtacc tcctcccct taccccatt ccttttctgt acctagcggg     1740
atacaggaag aagctaggac tgaggctttg tcagctgaaa agtgactttg gaagtaacag   1800
acaatgttta gaccatggaa actgcagagc tgacacatct tgaatctccc tttagctttc   1860
agctaggcca gaaaggagag ttctagaacc cagcaggacc ttagctgcct gggagctcct   1920
tccttctctc cccgctgcag tgctcaggga gggaacgaaa agcagctgat cttagaaatt   1980
aagtcctaag tgttatgtat gtaaggaaag acattggtgc tataatgaag acgagccaag   2040
gctcaaagaa agatggcttc cctagacaaa gaagaacaca ggattattca aggactttgg   2100
aggagaaact cagagtagac tcaaattgaa caagcccagt gactccccat tctgcagaag   2160 tgggggggg gggcggattt cagtaccata aaagggcacc ggatctcctg ggtgtccagt   2220
tgggcaggtt tctccctgcc aaggctaccg acagagggg ctcatagagg ctgaggtcca   2280
gcctgtgccc tgctctctag gctgcacatc ctgatgtggg cagggtctgc ccagagtaag   2340 gaatgyctttt cctaattygc acaaaggtac tgtgtgcact tcagtggtc ctgaggagga   2400 ccttaaggca tgtgtataag cctttgtgtt tttctgctca gatgacctgg agatattacc   2460
tcttcttggc cacaatcatt tttctcaggg tctataccat agttcgtctg ctaagaaagt   2520
```

-continued

```
gggtttctgt ttgcaaggag aggggaccca agtaatgaat atgaagactg gttctgaggg      2580
tgggcttgat tatttgtgaa gcccagcctt cctacatccc accctccctg cagtttagat      2640
gtgtgtggga catatgtggt cttccccttt cctggatcaa ggctatgaca ggcaggcttc      2700
tggtatgtgc ttggtacatg tgctgcaata catgtgcttg atggtacatg cgtgcccctc      2760
cccatacaga accttgtact tcagttatct ttaacataac ttagtagact ttccatctgt      2820
cctaaggcat gactgtcagc ttcagcaacc ttgctaggtg caggctgggt accctgtggc      2880
ctgagaactg agcccagagt ttgacctgaa cattgagcct ggaccaggca gaagctggtc      2940
agaatgtact gtctccattt tgggccaagc cgggaccaaa cttactaact caggcaagcc      3000
agggtgaaac ttaaaccctc ttttatcttt aacctgaatc caggctggag ttgaagctca      3060
atgataaagg gcttgcctgt cggtcaagag accctcggat ggatcccagg actgtaaaaa      3120
aaaaataaat aaaaatatgc ccccctctctc caacctcttg gaggcagctg gcagcccagc      3180
tcaaggaggc aagaggttcc ccctggctgc ttgctttaat tggccggtga tctctgcctg      3240
gtgaattggt tttatagtct ctgagtccag cccctggaca acccccycyc ctttgcctct      3300
ccagaactcc aggagcttgg ctgtctctag tgaagagtgg agattcagat tctgagggag      3360
ggagggaggg tctgacctgt gtggtgacct gtaaccagct gaaggcaaca ggcttttgtg      3420
gtgtgctgag gatgggggt gggagaagag ctggaaaact ctgtagaaat gccctagagg      3480
aacagaagcc ctgtattcag gggccaaact gctctactaa ttcacaatcc ccaggaggca      3540
tttctaaaag ccagtgaaca gatctggaga ggaacatccc ccagtcccgt cactgactcc      3600
cccagggaga ctggggtggt acgcaggaga gtgggggag ggtgggcact ttgcctggcc      3660
ctgtctctct gtttcaaagt ttggctgtgc tgttcaaatg tccccaaagg ccttgtcttg      3720
ctcaatcaga ggtggaaaaa gatcacctcc cggtgacctc cttcaggccc caggggatgg      3780
gctgtgtcca gagctatgtg gcagagcttg tttccagagc ccagagagc cccgctggcc      3840 tgccttgctg ccccagtggc gaaacgcaag cccaacactg agcatggcag ggagtgggtg      3900
ttggggacag tctagccaag gcccctgtct gtcccaagct ttccaggaac taagcagtga      3960
ggtcactgtg acagtcctgc ctggtcagcg aggagaatat tctgagcttt cccgctctgg      4020
gacttactgg ggaggggcg ggtaccagtg tatggagtaa caagacatca gccttcgtgg      4080
ctctgcagga tttgggggaa tcagtacagt ggccactgtg gctgctatga agataaggcc      4140
ttttggagac aggctatcct ggcctgatac cctggttgga cctagaggga tacagggtgg      4200
agccacagtc atttcaagtt ccctggggtt cctgtgggct gcagacctag ggacagagc      4260 ctcaaggaag acagcagaac aaagctgagc tcttccatat atgccagctt tggccaaggt      4320
gctatgaggt ctgtgacccc aggcttgcac tgccccttc tctacagttg tctgatgtcc      4380
accccatctc tgggttcaca gaaactgaca cggggagacc cagcgagatg tagcatttcc      4440
ttcatcccca gtctggttgg cccggggtct gggcatcctg ccttaaggaa aggaatgggg      4500
accattattt tttaacctgt atataatatt tgacctttt ttggttcttt atatgtatac      4560
atgtgtaaat atcctctcat ccatcaagtg gtacagtttt taataaaacc atttaaagca      4620 aaaaaaaaa aaaaaactc gagagtactt ctagagcggc cgcgggccca tcgattttcc      4680
acccggaa                                                              4688
```

<210> SEQ ID NO 2
<211> LENGTH: 185
<212> TYPE: PRT
<213> ORGANISM: mouse

<400> SEQUENCE: 2

| | | | | | | | | | | | | | | |
|---|---|---|---|---|---|---|---|---|---|---|---|---|---|---|
|Met|Glu|Pro|Pro|Gln|Cys|Val|Glu|Glu|Leu|Glu|Asp|Asp|Val|Phe|Gln|
|1| | | |5| | | | |10| | | | |15| |

Ser Glu Asp Gly Glu Pro Gly Thr Gln Pro Gly Gly Leu Leu Ser Ala
        20                25              30

Asp Leu Phe Ala Gln Ser Gln Leu Asp Cys Pro Leu Ser Arg Leu Gln
      35                40                  45

Leu Phe Pro Leu Thr His Cys Cys Gly Pro Gly Leu Arg Pro Ile Ser
    50                55              60

Gln Glu Asp Lys Ala Thr Gln Thr Leu Ser Pro Ala Ser Pro Ser Gln
65              70                75              80

Gly Val Met Leu Pro Cys Gly Val Thr Glu Glu Pro Gln Arg Leu Phe
            85              90              95

Tyr Gly Asn Ala Gly Tyr Arg Leu Pro Leu Pro Ala Ser Phe Pro Ala
        100              105            110

Gly Ser Pro Leu Gly Glu Gln Pro Pro Glu Gly Gln Phe Leu Gln His
      115              120              125

Arg Ala Glu Val Gln Ile Ala Arg Lys Leu Gln Cys Ile Ala Asp Gln
        130              135            140

Phe His Arg Leu His Thr Gln Gln His Gln Asn Arg Asp Arg Ala
145              150              155            160

Trp Trp Gln Val Phe Leu Phe Leu Gln Asn Leu Ala Leu Asn Arg Gln
            165              170            175

Glu Asn Arg Glu Gly Val Gly Pro Trp
        180              185

<210> SEQ ID NO 3
<211> LENGTH: 4959
<212> TYPE: DNA
<213> ORGANISM: human

<400> SEQUENCE: 3

| | | | | | |
|---|---|---|---|---|---|
|gaacgatact|agtggaccca|aagaattcgg|cacgagctcg|tgttttaatt|cggcacgagc|60|
|cgcaccgtgc|ggagtggcct|cctcccgccc|cggcctgtgc|ccgccgccgc|cgccgcccct|120|
|gcctgcgcct|cccgcctcct|gccgcagccc|gctgggcttt|tcccctcctt|cccaatcgag|180|
|tctgggcgtc|cagcccccga|gtgctcgtca|cgctggaccc|tggcgcggag|ccctggcatc|240|
|acgactcgga|ggccgagact|ctctcctgga|gtcacccagg|agagatggag|ccatctcagt|300|
|gtgtggagga|gctggaggat|gatgtgttcc|aaccagagga|tggggagccg|gtgacccaac|360|
|ccggagcttt|gctctctgct|gacctgtttg|cccagagcct|actggactgc|cccctcagcc|420|
|gacttcagct|cttccctctc|acccactgct|gtggccctgg|ccttcgaccc|accagccagg|480|
|aagacaaagc|tacccagact|ctcagcccag|cctcccccag|ccaaggtgtc|atgctgcctt|540|
|gtggggtgac|tgaggaaccc|cagcgactct|tttatggcaa|tgctggctat|cggcttcctc|600|
|tccctgccag|tttcccagca|gtcttgccca|ttggggagca|gccccccgaa|gggcagtggc|660|
|aacatcaagc|agaggtacag|attgcccgaa|agcttcagtg|cattgcagac|cagttccacc|720|
|ggcttcatgt|gcagcaacac|cagcagaacc|aaaatcgtgt|gtggtggcag|atcctcctct|780|
|tcctgcacaa|ccttgctttg|aatggagaag|agaacaggaa|cggggcaggc|cctaggtgag|840|
|ggtgggctgc|cctcttcaca|tggggcacca|ggaacaccgt|ctggaacagg|aaggacatcg|900|
|ggcaggactg|acactgtgtc|ttgtgaaatt|gttttttgt|tgttattttg|tgttttaatt|960|

```
tttttttaatt tctctctgag tgtacataca acatactcaa gcgggacctt ctttctctgt    1020
caggcccttg acctggaatg ggggcctgtg tcaaacactg ttgaaggaga ggctgatgtg    1080
tctgtgatgg tgagaattcc caarggctct gacaagtaga ttcttcgact gaggaatcta    1140
ccagttgycg aagatgatcc gttagtgatg ttctctggga agtggactgt ggttttcca    1200 gaggaactca gttaagaaat cgagagtgga ttagactccc cagttccacc aaacctatga    1260
gccttccact gtggatgggg gccgtgatcc tgatggtcac attgctttaa cccagcaggg    1320
cttcggccag gggcttttcca cttgaggata gcagcttcac taggctggcc ggccagctcc    1380
acatctgact gggttcttac ttctcagcca gtacctgccc catgggctca aggattcctg    1440
gccagctcct gccacctcca gcagacctca gggagggttg ggtttctcta aggacccctc    1500
aaacatgtcg caaaatgaac caaacttctg gctaggcctc aaaactgact tggtcccact    1560
tggaggcccc aggattggtc ctgaggtaca gagccactgc caccactggc ggcctgggac    1620
cagctgggtg tcagccacgg atgagccgaa tagccagtca gcatgttgct gctggcagcc    1680
tgtgcctttg tcagctcttc tttcaaaaga ccccaccgac agaccgcatt ccaccccaa    1740 catcggcact gagggacatc gggggcaagt ttgcagtggg gccggaaaat atggtggcca    1800
ccctaccatg agagtcagcc gtaggggacc ccagacccct tggtttcctt ggaaacaaca    1860
tacctcttcc cccttatccc cagtcctttt tcatacctag tgggatacag aagaagccag    1920
gacagtggct ttgccagcta agtgactttt agagtaacag ataacgatta gagtggggaa    1980
ccgtcaaagc tgggtacaca tttcctatct tcctccagct tccagctagg ccagaagggc    2040
atgctctgga acccagcagg atcacagctg cctgtgcacg tcttcccttc tctccctgct    2100
gcggcactta tggagaggat ctaaagcagc cggtgtggca gctccgatag caggcacagg    2160
gaatctgtta accagacgct agaaactaaa ttataacttt tgcatatgtg agaaaagaca    2220
acattggtgc taacagtgaa gtaaggccca aggaaagacg gcttccctgg acaaagaaga    2280
cctcagggct acccaaggaa ataggaggag tctagagtag actcacaaat ctgaacaagc    2340
ccaagtcttc cagttctgag gagaggaggt cttcagtact attgaaggag acattgatct    2400
tctggatgta cagttgtgca ggttgttcac tgcacaaggg cacctgcagc taatggaggc    2460
tggaattcag cttgtgttct gctcactaag ctgtgtgcgt gccctggtgt ggggctactt    2520
ctcccaagaa gaagggggtgc ctttcctaat ttgcaaaggt gccatatggg ctcacagcac    2580
cctggaggag aagggcctca aactgtgcat gtaagccttt gttttgttct gctcagatat    2640
tctggatatt acctcttctt ggtcagaatt ctattctcag ggtgtgtacc atgatttgtc    2700
tgctaagaag acgggttcct gttttttgcag agaaggagcc ggggaccagc ttgaagactg    2760
gctctgggac acactgacca ttgtgaaatt cagccttccc tgtgggtctc ataccatt    2820 tatgatgtgt atgggacata cgttgttctc ccctctctgg atcaaggtgg tgacaggcag    2880
cctgctgccg tatgcttcag tggcacacac caaaaaaacc gggattattt acagcagcca    2940
ctattcaccc cttttggcag actctccacc tgagttcagt gagagagaaa atgatttaga    3000
tcttggtgct ggggcaaggc catcagcttc agagaccttg ccaggcccag gctgggtgcc    3060
ctgtggcctg agaactgagc ccagactttg acaaacccac ctcaacatca agcctgggc    3120 aggtggaagg tggtctgact gcactgtctc catcttatgc aaagccagga actcactcac    3180
tgtcttaagt gagccagggc aaaatttaca cccctcacgt ttccctctcc cttcttcccc    3240
accaacaaaa cccaggaggt agctggcaga gtagctgtca ggaaggagaa aggttctttc    3300
tggctggttg ttttttaattg gcttagtgat ctaaactggc cccttcctcc tctgcctggt    3360
```

```
gagttggcct aaacattcct caagtctagc ttcaggagac ctgcccctcc ccccgacct    3420 ccacccccct agactccatc ccccacccccc aggagcctgg ctgtctctag cgaggggtgg  3480
agaatcagat ttagagggag ggagagtctg acctggatcc tgacctgtaa ccagctgaag   3540
acggtggagg ctttgtggct tgctgagggt gggggttggg agagggactg gaaaccttcc   3600
tcctcgggaa agaaatgcct gggaggaagg gaagcctgat attcagggtc aaaacagccc   3660
ttctaattca aaccccaaa gcaggggttt ctagaagttg gtcaacagat ctggtgaggg    3720
aagtccccag gccagacgct ggactcctgc aatgagggtg gaggactcag cctggcctct   3780
gcctggcctg tttcaaagtc tgggccactg gcagccttct cttgctcaat ccgaggtgga   3840
aaaagatcac cctcccagtg acctcccctc agccccagg ggagtaggtc tgtgtccgaa    3900
gctatgtggc aggcttgttt gaaggaccca gaggggccca gctgacctgt ctcactgctc   3960
ctggcagccc agcccatcg gcaggtggcc cctgcctggg ggttattcgg gacggttcag    4020
ccagggcctc ccaggaagag tgctgtggag ccacggtgac tgtcctggac agcaaggagc   4080
atgctacccc agtgagcact tctttttgag ggacttgatg gggaggtggg gtaggcagaa   4140
gggacgtggc agaagcggga agactttggt caccatggct ctgcaggcct tctgcaaatc   4200
agtgctggcc tgggcttgga accagttctt gtgtgtgaag gtgaggactc ttggaagcag   4260
gccatcctgg ccagacaccc gtagcagaag gggctcacct gtcacccttca ggcagcctga  4320 gggctggtgg ggacttttga gtcttgaggg gatagcggaa aaagctgagc tcataggtgc   4380
ccagccagcc tcccagctaa aggtgctcag agccccmctg ccccctctct ctgtgcaggt   4440
ggccagtgcc cctccctgct ctgggagcat tgctagcctt ctaccccatc cctggatcca   4500
caggggctat cgaggagacc cagtgagaat gtagcatttt gttcatcccc agggtagctg   4560 ccctgggggtc tgggcactct gcctctggga gagaggaaga agaaaggggc cccatttttt   4620
aaaaaactgt acagagcctt tggctttatg tgtttatgtt cttcacatgc atatgtgtgt   4680
atgtgtgtat atctttcccc ccatcaattg gtacaatttt taataaaatc atttaaagca   4740
aaaaaaaaaa aaaaaaactm ragaawamwt ctagagcggc cgcgggccca tcgattttcc   4800
acccgggtrg gtaccaggt tagtgtaccc aattcgccct atagtgagtc gtattacaat    4860
tcactggccg tcgttacaa cgtcgtgact gggaaaacct ggcgttacca acttaatcgc    4920
cttgagcaca tcccctttcg ccagctggcg taatagcga                          4959
```

<210> SEQ ID NO 4
<211> LENGTH: 183
<212> TYPE: PRT
<213> ORGANISM: human

<400> SEQUENCE: 4

```
Glu Pro Ser Gln Cys Val Glu Glu Leu Glu Asp Asp Val Phe Gln Pro
1               5                   10                  15

Glu Asp Gly Glu Pro Val Thr Gln Pro Gly Ser Leu Leu Ser Ala Asp
            20                  25                  30

Leu Phe Ala Gln Ser Leu Leu Asp Cys Pro Leu Ser Arg Leu Gln Leu
        35                  40                  45

Phe Pro Leu Thr His Cys Cys Gly Pro Gly Leu Arg Pro Thr Ser Gln
    50                  55                  60

Glu Asp Lys Ala Thr Gln Thr Leu Ser Pro Ala Ser Pro Ser Gln Gly
65                  70                  75                  80

Val Met Leu Pro Cys Gly Val Thr Glu Glu Pro Gln Arg Leu Phe Tyr
```

```
                    85                  90                  95
Gly Asn Ala Gly Tyr Arg Leu Pro Leu Pro Ala Ser Phe Pro Ala Val
            100                 105                 110
Leu Pro Ile Gly Glu Gln Pro Pro Glu Gly Gln Trp Gln His Gln Ala
        115                 120                 125
Glu Val Gln Ile Ala Arg Lys Leu Gln Cys Ile Ala Asp Gln Phe His
    130                 135                 140
Arg Leu His Val Gln Gln His Gln Asn Gln Asn Arg Val Trp Trp
145                 150                 155                 160
Gln Ile Leu Leu Phe Leu His Asn Leu Ala Leu Asn Gly Glu Glu Asn
                165                 170                 175
Arg Asn Gly Ala Gly Pro Arg
            180

<210> SEQ ID NO 5
<211> LENGTH: 54
<212> TYPE: DNA
<213> ORGANISM: mouse
<220> FEATURE:
<221> NAME/KEY: misc_feature
<222> LOCATION: ()..()
<223> OTHER INFORMATION: BH3 doman of mouse bmf

<400> SEQUENCE: 5
cagatcgcca gaaagcttca gtgtattgca gaccagttcc atcggcttca tacg         54

<210> SEQ ID NO 6
<211> LENGTH: 18
<212> TYPE: PRT
<213> ORGANISM: mouse
<220> FEATURE:
<221> NAME/KEY: misc_feature
<222> LOCATION: ()..()
<223> OTHER INFORMATION: BH3 doman of mouse bmf

<400> SEQUENCE: 6

Gln Ile Ala Arg Lys Leu Gln Cys Ile Ala Asp Gln Phe His Arg Leu
1               5                   10                  15

His Thr

<210> SEQ ID NO 7
<211> LENGTH: 54
<212> TYPE: DNA
<213> ORGANISM: human
<220> FEATURE:
<221> NAME/KEY: misc_feature
<222> LOCATION: ()..()
<223> OTHER INFORMATION: BH3 doman of human bmf

<400> SEQUENCE: 7
cagattgccc gaaagcttca gtgcattgca gaccagttcc accggcttca tgtg         54

<210> SEQ ID NO 8
<211> LENGTH: 18
<212> TYPE: PRT
<213> ORGANISM: mouse
<220> FEATURE:
<221> NAME/KEY: misc_feature
<222> LOCATION: ()..()
<223> OTHER INFORMATION: BH3 doman of human bmf

<400> SEQUENCE: 8

Gln Ile Ala Arg Lys Leu Gln Cys Ile Ala Asp Gln Phe His Arg Leu
1               5                   10                  15
```

His Val

<210> SEQ ID NO 9
<211> LENGTH: 2000
<212> TYPE: DNA
<213> ORGANISM: mouse
<220> FEATURE:
<221> NAME/KEY: misc_feature
<222> LOCATION: ()..()
<223> OTHER INFORMATION: bmf promoter

<400> SEQUENCE: 9

```
actctgacca gctcagacat gcacttttgg ccaagcctct gggtaaaata atatacctcc        60
ttttggctta gtgccttttg ctggaaatct atcaatttcg ggggactgtg ctactggcta       120
accttgactc cccactcttt ccctttccc  tctttgtcct ttggagacag tattttccta       180
ttctagcaac cacagccctc aatatggctg gttcattctg tttcaggtga cttctgaggg       240
agcaaaggaa agaatgatgg gaaaaaggta caaggagact tcaggctcta ttgggctgaa       300
ggtcccagct ccactgaact taaatctaag tttacaaccc agagagcagc tcggtggtca       360
gagcactgct gagccctact gccctggtg  ggtcagggtt gttgcaggac tggctccctc       420
tcactgctct ctggactcat cattttatct ttcctaaaac tcaggcttgg tcaagtcact       480
catctccaat aaaatctttg ctgcctcccc tttataaaat acagattctt cagtctggca       540
ttccagggac acctctgtag tctgacctga acccacctgc ccatgcctac cgttcgtaaa       600
tctcagtgtg cacccaatga tccagtcacc aagcctccct ctgctccctg cacaggtaag       660
ctctccagct cagcacttca gtctgctacc cttaggcctg gctattctt  ttttatttta       720
ttttattttt attttttga  gacggagtct cattgtcgcc caggctggag tgcggtggcg       780
ctatctccgc ccactgcaac cttcacctcc taggttcaag caattctcct acctcagcct       840
cccaagtagc tgggattaca ggcatgcgcc accacgcccg cctgattttt gtatttttag       900
tagagacagg gtttcccgtg ttggccaggc tggtctccaa ccactgagct caagtgaacc       960
acccgcctcg gcctcccaaa gtgttgggat tacaggcgtg agacatgtgc atctggtttt      1020
ccttattgaa aaatatttcc cattcaattt aaaagctgtc tccctgaggc cttctccagc      1080
cttttgtattc tgaattttc  tgcattcctc aatagtcatt atccttggaa tgaatacaat      1140
tccataact  tttcactatt ttcagggcta cctctcctag tagactgtaa gctccttgag      1200
ggcagacgcc aggtttctgg cactcagccc aatatctggc acagagtagg tgctcggtaa      1260
atgcctgtga agtagcccat agactccctt acgcggtctg caggacatgc tgctctcctg      1320
gcagcaccag cacagtctct aaatgctgcc atatgcgaga tatgtgtcaa ccgctcaagc      1380
agccccggcc ttcttgagcg ctccgcttct cagccaggtg cttattttgc cagtgcccac      1440
gcccagtcaa gaagaggacc taagggctcc cctggatgtg tttgtttcaa acacaccttc      1500
agctttggag ctgcagtttt cttccgacct gctcggcagg cgggagggag ctttcccctg      1560
aggctgggat cccataggga cccgcaccct gcacctgca  cccactggac gcaccagcct      1620
cataaaaaaa ctccccgcct ccttcccccc tccctttgtg gacgcgcagc aattattctg      1680
cccattgccg tgaaaagaa  gacaaaagtt actttggcgc ccctctcccc acacctaata      1740
cagaggattc agggactctc tggcgcttcc agagcctgtg ttagggacag aatccgcact      1800
ggcgacggcg ctccgactgc gcttctggcg acgtcggaa  ttttgctcgg ccccttgcaa      1860
tgtttccatg ggaaggttcg tacattcgtg accgtccctg gcagcggccc agcccgggac      1920
```

-continued

| | |
|---|---|
| ttggcgcttc actcgccatt ggtcagtcct cggcgtgacg cgcagggggg cggggcctca | 1980 |
| tcagctgttt gcgggatgcc | 2000 |

<210> SEQ ID NO 10
<211> LENGTH: 1833
<212> TYPE: DNA
<213> ORGANISM: human
<220> FEATURE:
<221> NAME/KEY: misc_feature
<222> LOCATION: ()..()
<223> OTHER INFORMATION: bmf promoter

<400> SEQUENCE: 10

| | |
|---|---|
| ctagtgtttg gttctcagca cccacatggt ggctcacacc catccttaac tccaatttca | 60 |
| ggagattcca cccctctta tagtcccctt gggcatcagg cacacacctg gtacacacac | 120 |
| atgcatgaag gcaaaacacc cacacgaata agtaaaaat aaatatatct aaaaacaatt | 180 |
| aaaaagaaa aacagaaaga aagaaaccaa agtaaataaa taaaaatttt aaaacaaaaa | 240 |
| atagccaaag acaattgagt ctgggagccc cagatccagc cagcttgtat cttagagcag | 300 |
| actgtaagta gagactgtaa ctaagcccag cttctctgct ttgcccgtgt ctctattgca | 360 |
| gctcatttag gttgtggcag ggctctgttc ctttcactga tttctgcctc cccactcagt | 420 |
| tttccccaaa attcatcttc tgtaaaatct ttgctaccag tcctctataa agtaattcct | 480 |
| tggggctgaa gagatggctc aagtgggtaa agcactggt tgctcttcca gaggacccag | 540 |
| gttcaattcc aagaactcac acggcagttc atagctgtct gtaactctgg ttccggatga | 600 |
| cacgctgtca caaagacata catacaggcg aaacactaac gcacataaaa taaaaattaa | 660 |
| caaattactt ttaaaaaata cagactcctc agcctggtat tccagggggc acctctgcaa | 720 |
| tctgacctga atctacctgc ccataccctc acatcctaaa tcatagtgaa gatgccagag | 780 |
| agcttgatgg ggggaggg ggacggggg ggcgtgcagc tgatcttgct ttccagacat | 840 |
| gttaagtact ttattctagc tccctgacct ctctgggtca ggactgtttt atttggtttt | 900 |
| tatttagtga aatattcccc attcttcaag gcccgactca aaaatctttg cttattatcc | 960 |
| ctaaaatagc accattcaag ctggtttcca tcattcacat gtgaagtatc ggttcattga | 1020 |
| ggtcaggcac cagaagtcta gcacttagac caggacctgg cacatagtag gtgttcaaaa | 1080 |
| aaatgtggag tcatccctag attggccata gtacacgaga tgcgttttgc tttcttagca | 1140 |
| gtccaagaac agccttctgc tgctgccata gatagggctg tccgagctac ccctttgatt | 1200 |
| tcccctctgc tagagtcctt ttttcaacag tgatcttcca cagtctagaa gagaggacat | 1260 |
| ggcctttctt ttgcacttga tggatccgaa tgtcatttgg ttctagatgc agacacacgt | 1320 |
| gttctcctcc agctttcctc agacacgccc aacaggaaag agggcagttt tttgttttgg | 1380 |
| tttttatt gttttgcttt tttttatta gggaccagca gctcggtttt ttttttttc | 1440 |
| cgctatatat tacaaggcgc gtctgaaaac tcccagtctc ctcctgagcc ggcttttgg | 1500 |
| aagtcctgca ataactcagc ccatttccaa gtagacaaaa gtcacttagg cgtcttgtcc | 1560 |
| ccccactacc tagtagaaaa cctagggact ctctgtcgtt tctggggctt gcattaggaa | 1620 |
| ccgaatcctc accctctaca gcgctccaat tgcgcttctg acggaggtca gaaatgcgcc | 1680 |
| cggccccta taatgtttcc aagggaaggt ttgtacattg gtgattgtcc ctggcagctg | 1740 |
| cccagcttga gacttggacc tccacttgcc attggtcagt ggttggagtg acgcaaagag | 1800 |
| gggcggggcc tcatcagctg tttgcgggat gcc | 1833 |

```
<210> SEQ ID NO 11
<211> LENGTH: 21
<212> TYPE: DNA
<213> ORGANISM: artificial sequence
<220> FEATURE:
<221> NAME/KEY: misc_feature
<222> LOCATION: ()..()
<223> OTHER INFORMATION: 5' sense primer

<400> SEQUENCE: 11
ccggatggat caccaggaat g                                          21

<210> SEQ ID NO 12
<211> LENGTH: 19
<212> TYPE: DNA
<213> ORGANISM: artificial sequence
<220> FEATURE:
<221> NAME/KEY: misc_feature
<222> LOCATION: ()..()
<223> OTHER INFORMATION: 3' antisense primer

<400> SEQUENCE: 12
cagagctgac aaaggcaag                                             19

<210> SEQ ID NO 13
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: internal bmf primer

<400> SEQUENCE: 13
ccacttcctg gagaacatca                                            20

<210> SEQ ID NO 14
<211> LENGTH: 25
<212> TYPE: DNA
<213> ORGANISM: artificial sequence
<220> FEATURE:
<221> NAME/KEY: misc_feature
<222> LOCATION: ()..()
<223> OTHER INFORMATION: 5' sense primer

<400> SEQUENCE: 14
tgatgacatc aagaaggtgg tgaag                                      25

<210> SEQ ID NO 15
<211> LENGTH: 23
<212> TYPE: DNA
<213> ORGANISM: artificial sequence
<220> FEATURE:
<221> NAME/KEY: misc_feature
<222> LOCATION: ()..()
<223> OTHER INFORMATION: 3' antisense primer

<400> SEQUENCE: 15
tccttggagg ccatgtaggc cat                                        23

<210> SEQ ID NO 16
<211> LENGTH: 22
<212> TYPE: DNA
<213> ORGANISM: artificial sequence
<220> FEATURE:
<221> NAME/KEY: misc_feature
<222> LOCATION: ()..()
<223> OTHER INFORMATION: internal primer
```

-continued

<400> SEQUENCE: 16
cccggcatcg aaggtggaag ag          22

<210> SEQ ID NO 17
<211> LENGTH: 185
<212> TYPE: PRT
<213> ORGANISM: mouse
<220> FEATURE:
<221> NAME/KEY: misc_feature
<222> LOCATION: ()..()
<223> OTHER INFORMATION: predicted amino acid sequence of mouse Bmf

<400> SEQUENCE: 17

Met Glu Pro Pro Gln Cys Val Glu Glu Leu Glu Asp Asp Val Phe Gln
1               5                   10                  15

Ser Glu Asp Gly Glu Pro Gly Thr Gln Pro Gly Gly Leu Leu Ser Ala
            20                  25                  30

Asp Leu Phe Ala Gln Ser Gln Leu Asp Cys Pro Leu Ser Arg Leu Gln
        35                  40                  45

Leu Phe Pro Leu Thr His Cys Cys Gly Pro Gly Leu Arg Pro Ile Ser
    50                  55                  60

Gln Glu Asp Lys Ala Thr Gln Thr Leu Ser Pro Ala Ser Pro Ser Gln
65                  70                  75                  80

Gly Val Met Leu Pro Cys Gly Val Thr Glu Glu Pro Gln Arg Leu Phe
                85                  90                  95

Tyr Gly Asn Ala Gly Tyr Arg Leu Pro Leu Pro Ala Ser Phe Pro Ala
            100                 105                 110

Gly Ser Pro Leu Gly Glu Gln Pro Pro Glu Gly Gln Phe Leu Gln His
        115                 120                 125

Arg Ala Glu Val Gln Ile Ala Arg Lys Leu Gln Cys Ile Ala Asp Gln
    130                 135                 140

Phe His Arg Leu His Thr Gln Gln His Gln Asn Arg Asp Arg Ala
145                 150                 155                 160

Trp Trp Gln Val Phe Leu Phe Leu Gln Asn Leu Ala Leu Asn Arg Gln
                165                 170                 175

Glu Asn Arg Glu Gly Val Gly Pro Trp
            180                 185

<210> SEQ ID NO 18
<211> LENGTH: 184
<212> TYPE: PRT
<213> ORGANISM: human
<220> FEATURE:
<221> NAME/KEY: misc_feature
<222> LOCATION: ()..()
<223> OTHER INFORMATION: predicted amino acid sequence of human Bmf

<400> SEQUENCE: 18

Met Glu Pro Ser Gln Cys Val Glu Glu Leu Asp Asp Val Phe Gln
1               5                   10                  15

Pro Glu Asp Gly Glu Pro Val Thr Gln Pro Gly Ser Leu Leu Ser Ala
            20                  25                  30

Asp Leu Phe Ala Gln Ser Leu Leu Asp Cys Pro Leu Ser Arg Leu Gln
        35                  40                  45

Leu Phe Pro Leu Thr His Cys Cys Gly Pro Gly Leu Arg Pro Thr Ser
    50                  55                  60

Gln Glu Asp Lys Ala Thr Gln Thr Leu Ser Pro Ala Ser Pro Ser Gln
65                  70                  75                  80

```
Gly Val Met Leu Pro Cys Gly Val Thr Glu Glu Pro Gln Arg Leu Phe
                85                  90                  95

Tyr Gly Asn Ala Gly Tyr Arg Leu Pro Leu Pro Ala Ser Phe Pro Ala
                100                 105                 110

Val Leu Pro Ile Gly Glu Gln Pro Pro Glu Gly Gln Trp Gln His Gln
                115                 120                 125

Ala Glu Val Gln Ile Ala Arg Lys Leu Gln Cys Ile Ala Asp Gln Phe
                130                 135                 140

His Arg Leu His Val Gln Gln His Gln Asn Gln Asn Arg Val Trp
145                 150                 155                 160

Trp Gln Ile Leu Leu Phe Leu His Asn Leu Ala Leu Asn Gly Glu Glu
                165                 170                 175

Asn Arg Asn Gly Ala Gly Pro Arg
                180

<210> SEQ ID NO 19
<211> LENGTH: 15
<212> TYPE: PRT
<213> ORGANISM: mouse/human
<220> FEATURE:
<221> NAME/KEY: misc_feature
<222> LOCATION: ()..()
<223> OTHER INFORMATION: partial amino acid sequence of Bmf

<400> SEQUENCE: 19

Ile Ala Arg Lys Leu Gln Cys Ile Ala Asp Gln Phe His Arg Leu
1               5                   10                  15

<210> SEQ ID NO 20
<211> LENGTH: 15
<212> TYPE: PRT
<213> ORGANISM: mouse/human
<220> FEATURE:
<221> NAME/KEY: misc_feature
<222> LOCATION: ()..()
<223> OTHER INFORMATION: partial amino acid sequence of Bim

<400> SEQUENCE: 20

Ile Ala Gln Glu Leu Arg Arg Ile Gly Asp Glu Phe Asn Ala Tyr
1               5                   10                  15

<210> SEQ ID NO 21
<211> LENGTH: 15
<212> TYPE: PRT
<213> ORGANISM: mouse/human
<220> FEATURE:
<221> NAME/KEY: misc_feature
<222> LOCATION: ()..()
<223> OTHER INFORMATION: partial amino acid sequence of EGL-1

<400> SEQUENCE: 21

Ile Gly Ser Lys Leu Ala Ala Met Cys Asp Asp Phe Asp Ala Gln
1               5                   10                  15

<210> SEQ ID NO 22
<211> LENGTH: 15
<212> TYPE: PRT
<213> ORGANISM: mouse/human
<220> FEATURE:
<221> NAME/KEY: misc_feature
<222> LOCATION: ()..()
<223> OTHER INFORMATION: partial amino acid sequence of Bak

<400> SEQUENCE: 22

Val Gly Arg Gln Leu Ala Ile Ile Gly Asp Asp Ile Asn Arg Arg
```

-continued

```
<210> SEQ ID NO 23
<211> LENGTH: 15
<212> TYPE: PRT
<213> ORGANISM: mouse/human
<220> FEATURE:
<221> NAME/KEY: misc_feature
<222> LOCATION: ()..()
<223> OTHER INFORMATION: partial amino acid sequence of Bax

<400> SEQUENCE: 23

Leu Ser Glu Cys Leu Lys Arg Ile Gly Asp Glu Leu Asp Ser Asn
1               5                   10                  15

<210> SEQ ID NO 24
<211> LENGTH: 15
<212> TYPE: PRT
<213> ORGANISM: mouse/human
<220> FEATURE:
<221> NAME/KEY: misc_feature
<222> LOCATION: ()..()
<223> OTHER INFORMATION: partial amino acid sequence of Bid

<400> SEQUENCE: 24

Leu Ala Leu Arg Leu Ala Cys Ile Gly Asp Glu Met Asp Val Ser
1               5                   10                  15

<210> SEQ ID NO 25
<211> LENGTH: 15
<212> TYPE: PRT
<213> ORGANISM: mouse/human
<220> FEATURE:
<221> NAME/KEY: misc_feature
<222> LOCATION: ()..()
<223> OTHER INFORMATION: partial amino acid sequence of Bik

<400> SEQUENCE: 25

Leu Ala Leu Arg Leu Ala Cys Ile Gly Asp Glu Met Asp Val Ser
1               5                   10                  15

<210> SEQ ID NO 26
<211> LENGTH: 15
<212> TYPE: PRT
<213> ORGANISM: mouse/human
<220> FEATURE:
<221> NAME/KEY: misc_feature
<222> LOCATION: ()..()
<223> OTHER INFORMATION: partial amino acid sequence of Hrk

<400> SEQUENCE: 26

Thr Ala Ala Arg Leu Lys Ala Leu Gly Asp Glu Leu His Gln Arg
1               5                   10                  15

<210> SEQ ID NO 27
<211> LENGTH: 15
<212> TYPE: PRT
<213> ORGANISM: mouse/human
<220> FEATURE:
<221> NAME/KEY: misc_feature
<222> LOCATION: ()..()
<223> OTHER INFORMATION: partial amino acid sequence of Bad

<400> SEQUENCE: 27

Tyr Gly Arg Glu Leu Arg Arg Met Ser Asp Glu Phe Val Asp Ser
1               5                   10                  15
```